United States Patent [19]

Shiokawa et al.

[11] Patent Number: 5,204,346
[45] Date of Patent: Apr. 20, 1993

[54] PYRAZOLOPYRIDINE COMPOUNDS

[75] Inventors: Youichi Shiokawa, Osaka; Atsushi Akahane, Hyogo; Hirohito Katayama, Hyogo; Takafumi Mitsunaga, Hyogo, all of Japan

[73] Assignee: Fujisawa Pharmaceutical Co., Ltd., Osaka, Japan

[21] Appl. No.: 729,688

[22] Filed: Jul. 15, 1991

[30] Foreign Application Priority Data

Jul. 18, 1990 [GB] United Kingdom ............... 9015764

[51] Int. Cl.$^5$ ................ C07D 471/04; A61K 31/435
[52] U.S. Cl. ............................. 514/234.5; 514/253; 544/114; 544/238; 544/239
[58] Field of Search ..................... 514/234.5, 253; 544/114, 238

[56] References Cited

U.S. PATENT DOCUMENTS

| 4,024,255 | 5/1977 | Ellis ........................... 514/234.5 |
| 4,666,902 | 5/1987 | Zoller et al. ................. 514/234.5 |
| 4,738,961 | 4/1988 | Jojima et al. ................ 514/253 |
| 4,826,845 | 5/1989 | Kasztreiner et al. ......... 514/253 |
| 4,925,849 | 5/1990 | Shiokawa et al. ............ 546/121 |
| 4,960,780 | 10/1990 | Shiokawa et al. ............ 514/253 |
| 4,985,444 | 1/1991 | Shiokawa et al. ............ 544/238 |
| 4,994,453 | 2/1991 | Shiokawa et al. ............ 514/253 |

FOREIGN PATENT DOCUMENTS

| 0299209 | 1/1989 | European Pat. Off. . |
| 0379979 | 8/1990 | European Pat. Off. . |
| 2057438 | 4/1981 | United Kingdom . |

OTHER PUBLICATIONS

Williams, Med. Res. Reviews vol. 9, pp. 219–43 (1989).
Burger, Medicinal Chemistry, 2d ed., Interscience, NY, 1960, p. 42.

Primary Examiner—Donald G. Daus
Attorney, Agent, or Firm—Oblon, Spivak, McClelland, Maier & Neustadt

[57] ABSTRACT

There are disclosed 3 [2(substituted alkyl)-3-oxo-2,3-dihydropyridazin-6-yl]-2-aryl pyrazolo [1,5-a]-pyridines useful for treating maladies requiring an adenosine antagonist, and preparative processes.

5 Claims, No Drawings

PYRAZOLOPYRIDINE COMPOUNDS

The present invention relates to novel pyrazolopyridine compound and a pharmaceutically acceptable salt thereof.

More particularly, it relates to novel pyrazolopyridine compound and a pharmaceutically acceptable salt thereof, which are adenosine antagonists and possess various pharmaceutical actions such as cognitive enhancing action, analgesic action, locomotor action, antidepressant action, cerebral vasodilating action, diuretic action, cardiotonic action, vasodilating action, the action of increasing the renal blood flow, renal prophylactic effect, improvemental effect of renal function, enhanced lipolysis action, inhibited anaphylactic bronchoconstrictive action, accelerating action of the release of insulin, antiulcerative action, protective effect against pancreatitis, or the like, and so are useful as psychostimulant, analgesic, antidepressant, ameliorants of cerebral circulation, drug for heart failure, cardiotonic agent, antihypertensive agent, drug for renal insufficiency (renal failure), drug for renal toxicity, renal prophylactic agent, improvemental agent of renal function, diuretic, drug for edema, antiobesity, antiasthmatic, bronchodilater, drug for apnea, drug for gout, drug for hyperuricemia, drug for sudden infant death syndrome (SIDS), ameliorants of immunosuppresion action of adenosine, antidiabetic agent, antiulcerative agent, drug for pancreatitis, or the like, and further which are inhibitors of platelet aggregation, so are useful as drug for thrombosis, drug for myocardiac infarction, drug for obstruction, drug for arteriosclerosis obliterans, drug for thronbophlebitis, drug for cerebral infarction, drug for transient ischemic attack, drug for angina pectoris, or the like; to a process for preparation thereof, to a pharmaceutical composition comprising the same, and to a method for using the same therapeutically in human being and animals for the prevention and/or treatment of melancholia, heart failure, hypertension (e.g. essential hypertension, nephrogenous hypertension, etc.), renal insufficiency (renal failure) (e.g. acute renal failure, etc.), renal toxicity [e.g. renal toxicity (damage of kidney) induced by a drug such as cisplatin, gentamicin, FR-900506 (disclosed in EP-0184162), cyclosporins (e.g. cyclosporin A) or the like; glycerol; etc.], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc.), obesity, bronchial asthma, gout, hyperuricemia, sudden infant death syndrome, immunosuppresion, diabetes, ulcer such as peptic ulcer (e.g. gastric ulcer, duodenal ulcer, etc.), pancreatitis, myocardiac infarction, thrombosis (e.g. arterial thrombosis, cerebral thrombosis, etc.), obstruction, arteriosclerosis obliterans, thrombophlebitis, cerebral infarction, transient ischemic attack, angina pectoris or the like.

Accordingly, one object of the present invention is to provide the novel pyrazolopyridine compound and a pharmaceutically acceptable salt thereof, which are useful as stated above.

Another object of the present invention is to provide processes for the preparation of the novel pyrazolopyridine compound or a salt thereof.

A further object of the present invention is to provide a pharmaceutical composition comprising, as an active ingredient, said pyrazolopyridine compound or a pharmaceutically acceptable salt thereof.

Still further object of the present invention is to provide a method for using said pyrazolopyridine compound as aforesaid therapeutic use, which comprises administering said pyrazolopyridine compound to human being or animals.

The novel pyrazolopyridine compound of the present invention can be shown by the following formula (I).

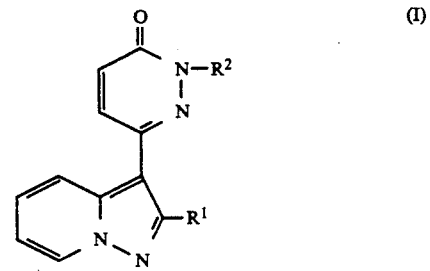

wherein
R$^1$ is aryl, and
R$^2$ is amino(lower)alkyl; lower alkylamino-(lower)alkyl; carboxy(lower)-alkylamino(lower)alkyl; protected carboxy(lower)alkylamino-(lower)alkyl; lower alkylamino-(lower)alkyl having hydroxy and aryloxy; protected amino(lower)alkyl; cyano(lower)alkyl; cyano(higher)alkyl; lower alkyl having heterocyclic group, in which heterocyclic group may have one or more suitable substituent(s); higher alkyl having heterocyclic group, in which heterocyclic group may have one or more suitable substituent(s); ar(lower)alkyl; lower alkenyl; or heterocyclic group which may have one or more suitable substituent(s).

The object compound (I) or a salt thereof can be prepared according to the following reaction schemes.

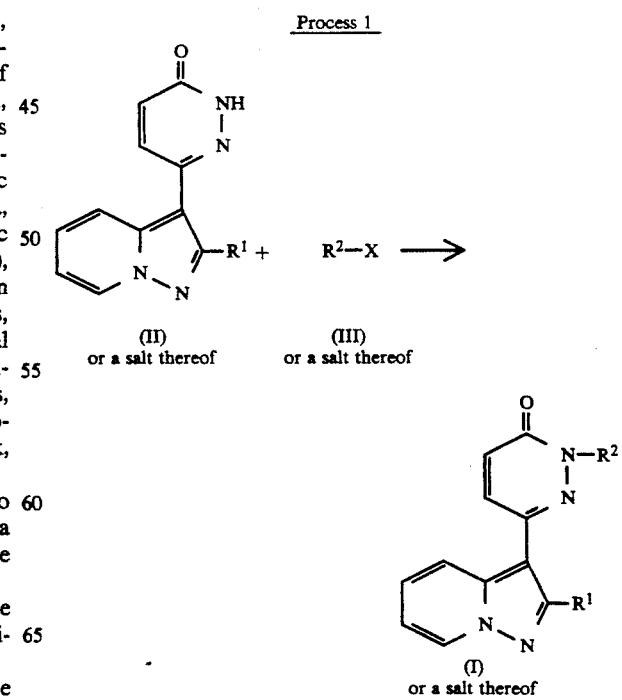

Process 2
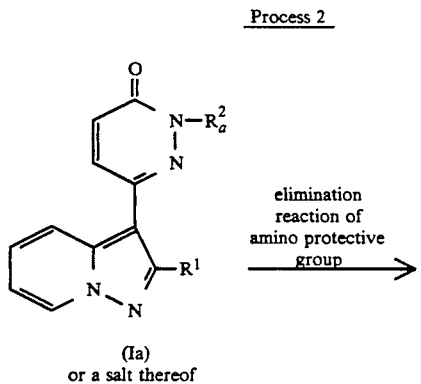
(Ia)
or a salt thereof
→ elimination reaction of amino protective group →
(Ib)
or a salt thereof
Process 3
(Ib)
or a salt thereof
+ R³—Y
(IV)
or a salt thereof
→
(Ic)
or a salt thereof
Process 4
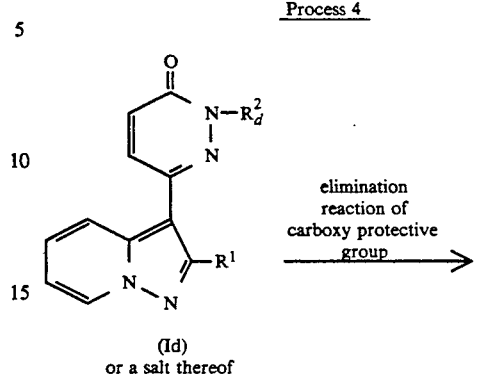
(Id)
or a salt thereof
→ elimination reaction of carboxy protective group →
(Ie)
or a salt thereof
Process 5
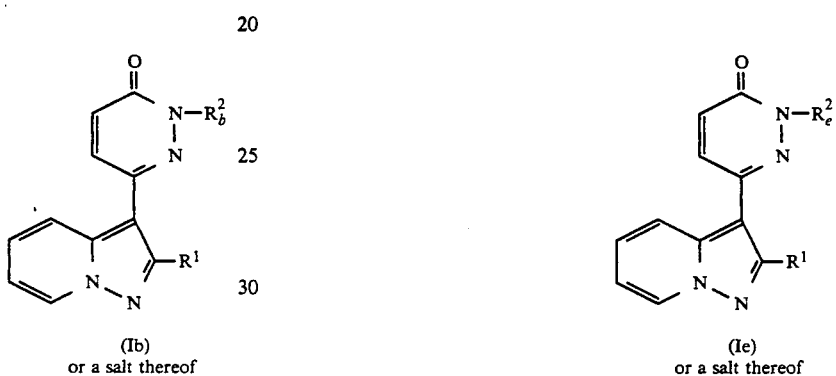
(Ib)
or a salt thereof
+ H—R⁴
(V)
→
(If)
or a salt thereof Process 6

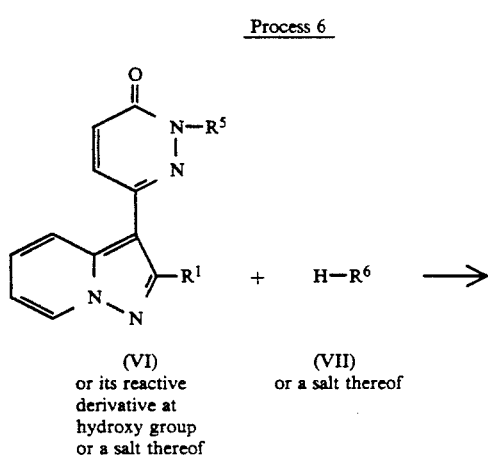

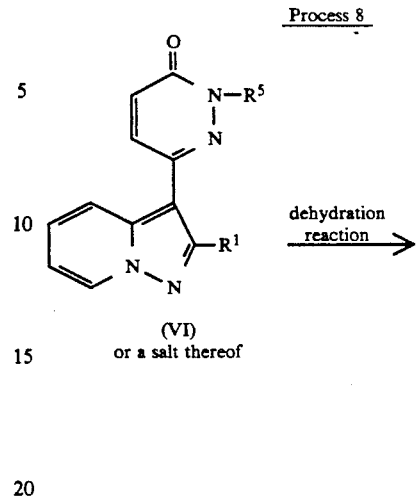

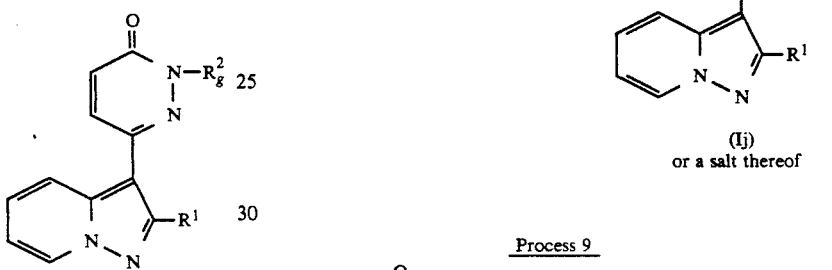

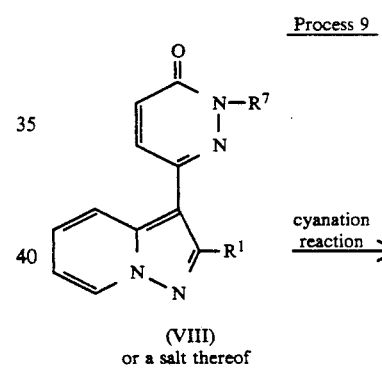

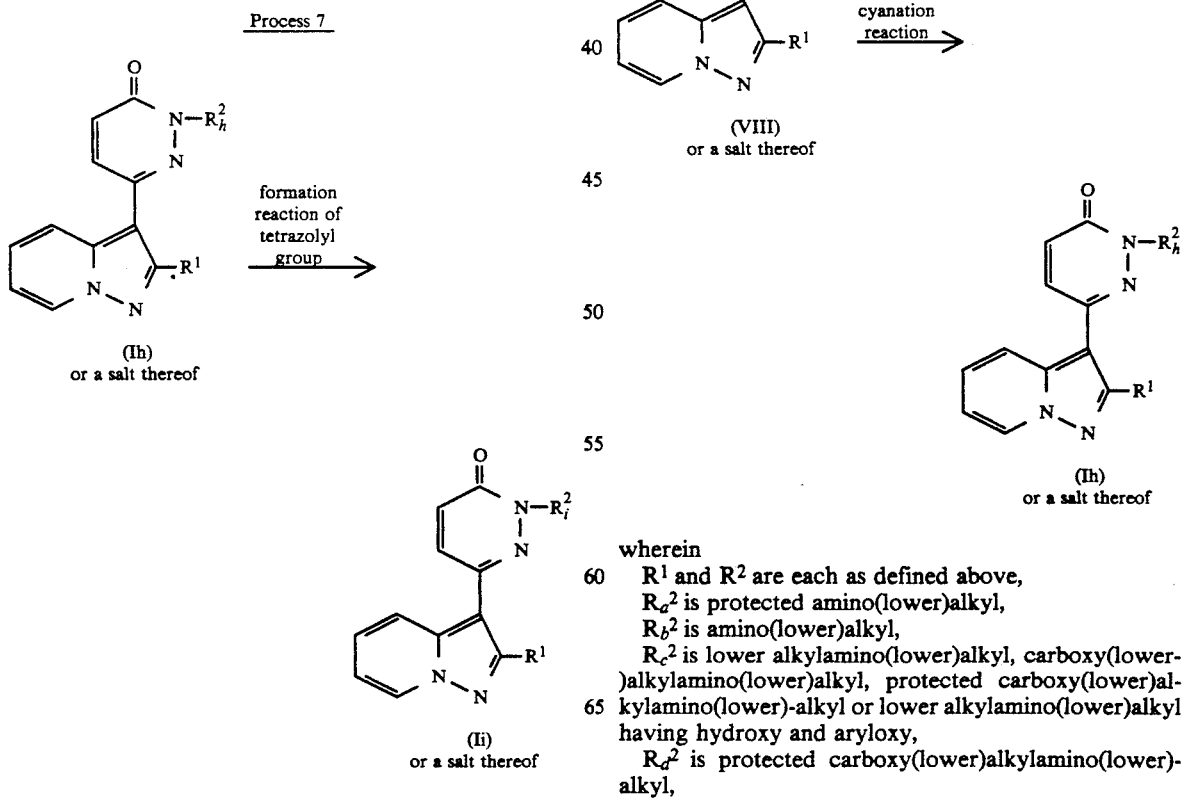

wherein
R$^1$ and R$^2$ are each as defined above,
R$_a^2$ is protected amino(lower)alkyl,
R$_b^2$ is amino(lower)alkyl,
R$_c^2$ is lower alkylamino(lower)alkyl, carboxy(lower)alkylamino(lower)alkyl, protected carboxy(lower)alkylamino(lower)-alkyl or lower alkylamino(lower)alkyl having hydroxy and aryloxy,
R$_d^2$ is protected carboxy(lower)alkylamino(lower)-alkyl, $R_e^2$ is carboxy(lower)alkylamino(lower)alkyl, $R_f^2$ is lower alkylamino(lower)alkyl having hydroxy and aryloxy, $R_g^2$ is amino(lower)alkyl; lower alkylamino(lower)alkyl; carboxy(lower)alkylamino(lower)-alkyl; protected carboxy(lower)alkylamino-(lower)alkyl; lower alkylamino(lower)alkyl having hydroxy and aryloxy; lower alkyl having a of the formula:

[in which

is N-containing heterocyclic group which may have one or more suitable substituent(s)]; or protected amino(lower)alkyl;

$R_h^2$ is cyano(lower)alkyl or cyano(higher)alkyl, $R_i^2$ is tetrazolyl(lower)alkyl or tetrazolyl(higher)alkyl, $R_j^2$ is lower alkenyl, $R^3$ is lower alkyl, carboxy(lower)alkyl, protected carboxy(lower)alkyl or lower alkyl having hydroxy and aryloxy, $R^4$ is lower alkyl having epoxy and aryloxy, $R^5$ is hydroxy(lower)alkyl, $R^6$ is amino; lower alkylamino; carboxy(lower)alkylamino; protected carboxy(lower)alkylamino; lower alkylamino having hydroxy and aryloxy; a group of the formula:

[in which

is as defined above]; or protected amino, $R^7$ is halo(lower) alkyl or halo(higher) alkyl, and X and Y are each a leaving group.

Among the starting compounds, the compounds (II), (VI) and (VIII) are novel.

The compound (II) can be prepared, for example, by the following reaction schemes.

Process A

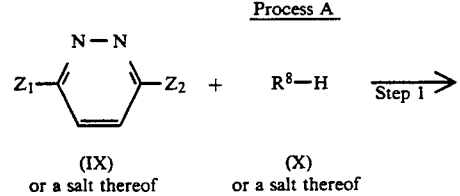

(IX) or a salt thereof       (X) or a salt thereof

-continued
Process A

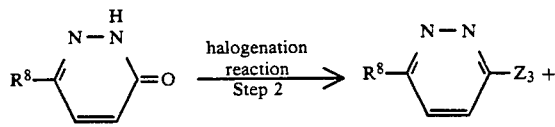

(XI) or a salt thereof       (XII) or a salt thereof

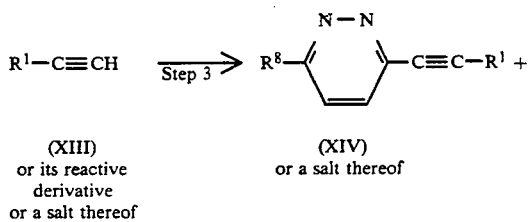

(XIII) or its reactive derivative or a salt thereof       (XIV) or a salt thereof

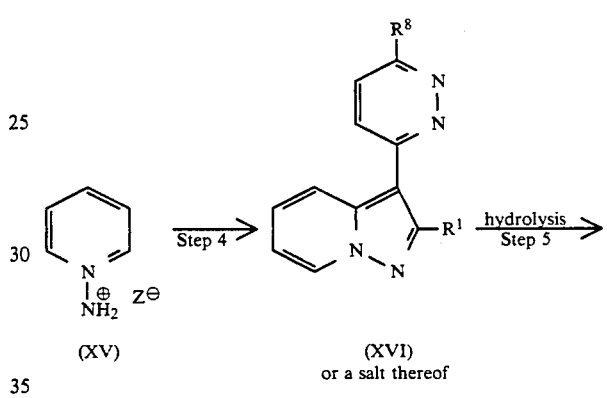

(XV)       (XVI) or a salt thereof

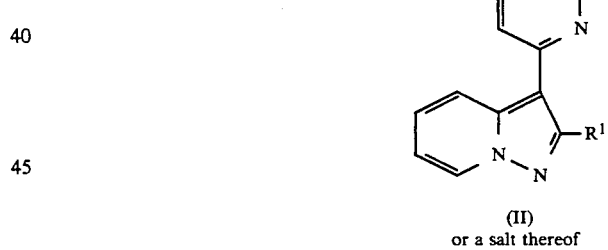

(II) or a salt thereof wherein $R^1$ is as defined above,
$R^8$ is arylsulfonyl which may have one or more suitable substituent(s), di(lower)alkylamino, lower alkoxy, lower alkylthio or acyloxy,
$Z_1$, $Z_2$ and $Z_3$ are each halogen, and
$Z^\ominus$ is an anion.

The compounds (VI) and (VIII) can be prepared according to the methods disclosed in Preparations described later or the similar manners thereto.

Suitable pharmaceutically acceptable salts of the object compound (I) are conventional ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumalate, methanesulfonate, benzenesulfonate, formate, toluenesulfonate, etc.), an inorganic acid salt (e.g. hydrochloride, hydrobromide, hydroiodide, sulfate, phosphate, etc.), a salt with an amino acid (e.g arginine, aspartic acid, glutamic acid, etc.), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

The term "higher" is intended to mean 7 to 20 carbon atoms unless otherwise indicated.

Suitable "aryl" may include phenyl, tolyl, xylyl, naphthyl and the like, in which the preferred one may be phenyl.

Suitable "amino(lower)alkyl" may include aminomethyl, 1-aminoethyl, 2-aminoethyl, 2-aminopropyl, 3-aminobutyl, 2-amino-1,1-dimethylethyl, 5-aminopentyl, 1-aminohexyl, and the like, in which the preferred one may be amino($C_1$-$C_4$)alkyl and the more preferred one may be 2-aminoethyl.

Suitable "lower alkylamino[lower)alkyl" may include mono- or di- (lower)alkylamino[lower)alkyl" such as methylaminomethyl, 2-(ethylamino)ethyl, 3-(propylamino)propyl, 2-(propylamino)butyl, 2-(t-butylamino)-1,1-dimethylethyl, 4-pentylaminopentyl, 6-hexylaminohexyl, dimethylaminomethyl, 2-dimethylaminoethyl, 1-(N-methylethylamino)ethyl, 1-dimethylaminopropyl, 2-diethylaminopropyl, 3-dimethylaminopropyl, 3-(N-propylbutylamino)butyl, 4-dimethylaminobutyl, 2-dibutylamino-1,1-dimethylethyl, 4-dipentylaminopentyl, 6-(N-pentylhexylamino)hexyl, or the like; and the like, in which the preferred one may be di(lower)alkylamino(lower)alkyl, the more preferred one may be di($C_1$-($C_4$)alkylamino($C_1$-($C_4$)alkyl and the most preferred one may be 2-dimethylaminoethyl, 3-dimethylaminopropyl and 4-dimethylaminobutyl.

Suitable "carboxy(lower)alkylamino(lower)alkyl" may include carboxymethylaminomethyl, 2-(carboxymethylamino)ethyl, 2-(1-carboxyethylamino)ethyl, 3-(2-carboxypropylamino)propyl, 2-(3-carboxypropylamino)butyl, 2-(2-carboxy-1,1-dimethylethylamino)-1,1-dimethylethyl, 4-(5-carboxypentylamino)pentyl, 6-(3-carboxyhexylamino)hexyl, and the like, in which the preferred one may be carboxy($C_1$-($C_4$)alkylamino($C_1$-($C_4$)alkyl and the most preferred one may be 2-(carboxymethylamino)ethyl.

Suitable "protected carboxy" in "protected carboxy[lower)alkylamino(lower)alkyl" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.]which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl(lower)alkyl ester [e.g. 2-mesylethyl ester, etc.]or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like.

Suitable example of "protected carboxy(lower)alkylamino(lower)alkyl" may be esterified carboxy(lower)alkylamino(lower)alkyl, in which the preferred one may be lower alkoxycarbonyl(lower)alkylamino(lower)alkyl such as methoxycarbonylmethylaminomethyl, 2-(ethoxycarbonylmethylamino)ethyl, 2-(1-ethoxycarbonylethylamino)ethyl, 3-(2-propoxycarbonylpropylamino)propyl, 2-(3-butoxycarbonylpropylamino)butyl, 2-(2-t-butoxycarbonyl-1,1-dimethylethylamino)-1,1-dimethylethyl, 4-(5-pentyloxycarbonylpentylamino)pentyl, 6-(3-hexyloxycarbonylhexylamino)hexyl, or the like; the more preferred one may be ($C_1$-$C_4$)alkoxycarbonyl($C_1$-$C_4$)alkylamino($C_1$-C4 )alkyl, and the most preferred one may be 2-(ethoxycarbonylmethylamino)ethyl.

Suitable "lower alkylamino(lower)alkyl having hydroxy and aryloxy" may be aforesaid "lower alkylamino(lower)alkyl" having "hydroxy" and "aryloxy" (e.g. phenoxy, tolyloxy, naphthyloxy, etc.) and suitable examples thereof may include 1-(1-naphthyloxy)-1-hydroxymethylaminomethyl, 2-(1-hydroxy-2-phenoxyethylamino)ethyl, 2-[2-hydroxy-3-(1-naphthyloxy)propylamino]ethyl, 2-[4-hydroxy-3-(p-tolyloxy)butylamino]propyl, 2-[4-hydroxy-1-(2-naphthyloxy)butylamino]-1,1-dimethylethyl, 4-[1-hydroxy-5-(1-nalphthyloxy)pentylamino]pentyl, 6-[2-hydroxy-4-(2-naphthyloxy,)hexylamino]hexyl, in which the preferred one may be ($C_1$-$C_4$)alkylamino($C_1$-$C_4$)-alkyl having hydroxy and naphthyloxy and the more preferred one may be 2-[2-hydroxy-3-(1-naphthyloxy)-propylamino]ethyl.

Suitable "protected amino(lower)alkyl" may be acylamino(lower)alkyl.

Suitable example of the acylamino may be lower alkanoylamino [e.g. formylamino, acetylamino, propionylamino, hexanoylamino, pivaloylamino, etc.], mono(or di or tri)halo(lower)alkanoylamino [e.g. chloroacetylamino, trifluoroacetylamino, etc.], lower alkoxycarbonylamino [e.g. methoxycarbonylamino, ethoxycarbonylamino, tert-butoxycarbonylamino, tert-pentyloxycarbonylamino, hexyloxycarbonylamino, etc.], mono(or di or tri)halo(lower)alkoxycarbonylamino [e.g. chloromethoxycarbonylamino, dichloroethoxycarbonylamino, trichloroethoxycarbonylamino, etc.], aroylamino [e.g. benzoylamino, toluoylamino, xyloylamino, naphthoylamino, etc.], ar(lower)alkanoylamino such as phenyl(lower)alkanoylamino [e.g. phenylacetylamino, phenylpropionylamino, etc.], aryloxycarbonylamino [e.g. phenoxycarbonylamino, naphthyloxycarbonylamino, etc.], aryloxy(lower)alkanoylamino such as phenoxy(lower)alkanoylamino [e.g. phenoxyacetylamino, phenoxypropionylamino, etc.], arylglyoxyloylamino [e.g. phenylglyoxyloylamino, naphthylglyoxyloylamino, etc.], ar(lower)alkoxycarbonylamino which may have suitable substituent(s) such as phenyl(lower)alkoxycarbonylamino which may have nitro or lower alkoxy [e.g. benzyloxycarbonylamino, phenethyloxycarbonylamino, p-nitrobenzyloxycarbonylamino, p-methoxybenzyloxycarbonylamino, etc.], thienylacetylamino, imidazolylacetylamino, furylacetylamino, tetrazolylacetylamino, thiazolylacetylamino, thiadiazolylacetylamino, thienylpropionylamino, thiadiazolylpropionylamino, lower alkylsulfonylamino [e.g. methylsulfonylamino, ethylsulfonylamino, propylsulfonylamino, isopropylsulfonylamino, pentylsulfonylamino, butylsulfonylamino, etc.], arylsulfonylamino [e.g. phenylsulfonylamino, tolylsulfonylamino, xylylsulfonylamino, naphthylsulfonylamino, etc.], ar(lower)alkylsulfonylamino such as phenyl(lower)alkylsulfonylamino [e.g. benzylsulfonylamino phenethylsulfonylamino, benzhydrylsulfonylamino, etc.], imide [e.g. 1,2-cyclohexanedicarboximide, succinimide, phthalimide, etc.], and the like.

Preferred example of said "protected amino(lower)alkyl" may be imido(lower)alkyl such as phthalimidomethyl, 2-phthalimidoethyl, 1-(1,2-cyclohexanedicarboximido)ethyl, 2-succinimidopropyl, 3-phthalimidobutyl, 2-(1,2-cyclohexanedicarboximido)-1,1-dimethylethyl, 5-phthalimidopentyl, 1-phthalimidohexyl, or the like, the more preferred one may be imido($C_1$-$C_4$)alkyl and the most preferred one may be 2-phthalimidoethyl.

Suitable "cyano(lower)alkyl" may include cyanomethyl, 1-cyanoethyl, 2-cyanoethyl, 3-cyanopropyl, 2-cyanobutyl, 4-cyanobutyl, 2-cyano-1,1-dimethylethyl, 4-cyanopentyl, 5-cyanopentyl, 6-cyanohexyl and the like, in which the preferred one may be cyano($C_1$-$C_6$)alkyl and the most preferred one may be cyanomethyl, 2-cyanoethyl, 3-cyanopropyl, 4-cyanobutyl, 5-cyanopentyl and 6-cyanohexyl.

Suitable "cyano(higher)alkyl" may include 7-cyanoheptyl, 8-cyanooctyl, 4-cyanooctyl, 8-cyano-3-methylheptyl, 9-cyanononyl, 1-cyanononyl, 10-cyanodecyl, 8-cyanoundecyl, 12-cyanododecyl, 11-cyano-4-methylundecyl, 13-cyanotridecyl, 6-cyanotetradecyl, 15-cyanopentadecyl, 12-cyanohexadecyl, 17-cyanoheptadecyl, 4-cyanooctadecyl, 19-cyanononadecyl, 1-cyano-12-ethylheptadecyl, 20-cyanoicosyl, and the like, in which the preferred one may be cyano($C_7$-$C_{16}$)alkyl and the more preferred one may be 7-cyanoheptyl, 8-cyanooctyl, 9-cyanononyl, 10-cyanodecyl and 12-cyanododecyl.

Suitable "lower alkyl" may be a straight or branched one such as methyl, ethyl, propyl, isopropyl, butyl, t-butyl, pentyl, hexyl or the like.

Suitable "lower alkenyl" may be a straight or branched one such as vinyl, allyl, 2-butenyl, 2-methyl-2-propenyl, 4-pentenyl, 3-hexenyl, or the like, in which the preferred one may be ($C_2$-$C_4$)alkenyl and the more preferred one may be vinyl.

Suitable "lower alkyl" in "lower alkyl having heterocyclic group, in which heterocyclic group may have one or more suitable substituent(s)" can be referred to the ones as exemplified before, and the preferred one may be ($C_1$-$C_6$)alkyl and the most preferred one may be methyl, ethyl, propyl, butyl, pentyl and hexyl.

Suitable "higher alkyl" in "higher alkyl having heterocyclic group, in which heterocyclic group may have one or more suitable substituent(s)" may include heptyl, octyl, 3-methylheptyl, nonyl, 2,6-dimethylheptyl, decyl, undecyl, dodecyl, 4-methyldodecyl, tridecyl, tetradecyl, pentadecyl, hexadecyl, heptadecyl, octadecyl, nonadecyl, 12-ethylheptadecyl, icosyl and the like, in which the preferred one may be ($C_7$-$C_{16}$)alkyl, and the more preferred one may be heptyl, octyl, nonyl, decyl, and dodecyl.

Suitable "heterocyclic group" in "lower alkyl having heterocyclic group, in which heterocyclic group may have one or more suitable substituent(s)" and "higher alkyl having heterocyclic group, in which heterocyclic group may have one or more suitable substituent[s)" means saturated or unsaturated, monocyclic or polycyclic heterocyclic group containing at least one heteroatom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.; saturated 3 to 8-membered heteromonocyclic group containing 1 to 4 nitrogen atom(s), for example, pyrrolidinyl, imidazolidinyl, piperidyl (e.g. piperidino, etc.), piperazinyl, etc.; unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.; unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.; saturated 3 to 8-membered heteromonocyclic group containing 1 to 2 oxygen atom(s) and 1 to 3 nitrogen atom(s), for example, morpholinyl, oxazolidinyl (e.g. 1,3-oxazolidinyl, etc.), etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.; saturated 3 to 8-membered heteromonocyclic group containing 1 to 2 sulfur atom(s) and 1 to 3 nitrogen atom(s), for example, thiazolidinyl, etc.; unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered heteromonocyclic group containing 1 to 2 oxygen atom(s), for example, furyl, pyranyl, dioxolyl, etc.; saturated 3 to 8-membered heteromonocyclic group containing 1 to 2 oxygen atom(s), for example, oxolanyl, tetrahydropyranyl (e.g. tetrahydro-2H-pyran-2-yl, etc.), dioxolanyl, etc.; unsaturated condensed heterocyclic group containing 1 to 2 oxygen atom(s), for example, isobenzofuranyl, chromenyl (e.g. 2H-chromen-3-yl, etc.), dihydrochromenyl (e.g. 3,4-dihydro-2H-chromen-4-yl, etc.), etc.; and the like.

Preferred example of "heterocyclic group" in "lower alkyl having heterocyclic group, in which heterocyclic group may have one or more suitable substituent(s)" and "higher alkyl having heterocyclic group, in which heterocyclic group may have one or more suitable substituent(s)" may be unsaturated 3 to 8-membered heteromonocyclic group containing 1 to 4 nitrogen atom(s); saturated 3 to 8-membered heteromonocyclic group containing 1 to 4 nitrogen atom(s); saturated 3 to 8-membered heteromonocyclic group containing 1 to 2 oxygen atom(s) and 1 to 3 nitrogen atom(s); and saturated 3 to 8-membered heteromonocyclic group containing 1 to 2 oxygen atom(s); in which the preferred one may be pyridyl, tetrazolyl, piperidyl, piperazinyl, morpholinyl, oxazolidinyl and tetrahydropyranyl; and the more preferred one may be 4-pyridyl, 1H-tetrazol-5-yl, piperidino, 1-piperazinyl, morpholino, 1,3-oxazolidin-5-yl and tetrahydro-2H-pyran-2-yl.

"Heterocyclic group" thus explained may have one or more (preferably 1 to 3) suitable substituent(s) such as hydroxy(lower)alkyl (e.g. hydroxymethyl, 2-hydroxyethyl, 1-hydroxypropyl, 4-hydroxybutyl, 2-hydroxy-1,1-dimethylethyl, 3-hydroxypentyl, 6-hydroxyhexyl, etc.), aryl which may have lower alkoxy (e.g. phenyl, naphthyl, 2-methoxyphenyl, 2-methoxynaphthyl, 3-ethoxyphenyl, 4-propoxyphenyl, 2-butoxyphenyl, 5-propoxynaphthyl, 3-t-butoxyphenyl, 4-pentyloxyphenyl, 2-hexyloxyphenyl, etc.), oxo, or the like, in which preferred "suitable substituent(s)" may be hydroxy($C_1$-$C_4$)alkyl, phenyl having ($C_1$-$C_4$)alkoxy and oxo, and the more preferred one may be 2-hydroxyethyl, 2-methoxyphenyl and oxo.

Suitable "heterocyclic group" in "heterocyclic group which may have one or more suitable substituent(s)" can be referred to the ones exemplified for "heterocyclic group" of "lower alkyl having heterocyclic group, in which heterocyclic group may have one or more suitable substituent(s)" and "higher alkyl having heterocyclic group, in which heterocyclic group may have one or more suitable substituent(s)", and the preferred one may be unsaturated condensed heterocyclic group containing 1 to 2 oxygen atom(s), the more preferred one may be dihydrochromenyl, and the most preferred one may be 3,4-dihydro-2H-chromen-4-yl.

This "heterocyclic group" may have one or more (preferably 1 to 4) suitable substituent(s) such as aforesaid lower alkyl, hydroxy, cyano or the like, in which the preferred one may be ($C_1$-$C_4$)alkyl, hydroxy and cyano, and the most preferred one may be methyl, hydroxy and cyano.

Suitable "ar(lower)alkyl" may include mono- or di- or tri- phenyl(lower)alkyl (e.g. benzyl, phenethyl, 2-phenylpropyl, 4-phenylbutyl, 2-phenyl-1,1-dimethylethyl, 1-phenylpentyl, 6-phenylhexyl, benzhydryl, trityl, etc.) and the like, in which the preferred one may be phenyl($C_1$-$C_4$) alkyl and the most preferred one may be benzyl.

Suitable "N-containing heterocyclic group" in "N-containing heterocyclic group which may have one or more suitable substituent(s)" may be heterocyclic group having at least one nitrogen atom as its ring member among the aforesaid "heterocyclic group", and said "N-containing heterocyclic group" may have one or more (preferably 1 to 3) suitable substituent(s) such as aforesaid hydroxy(lower)alkyl, aforesaid aryl which may have lower alkoxy, oxo or the like.

Suitable "tetrazolyl(lower)alkyl" may be 1H-tetrazol-5-ylmethyl, 2-(1H-tetrazol-5-yl)ethyl, 3-(1H-tetrazol-5-yl)propyl, 4-(1H-tetrazol-5-yl)butyl, 2-(2H-tetrazol-2-yl)-1,1-dimethylethyl, 4-(lH-tetrazol-1-yl)pentyl, 5-(1H-tetrazol-5-yl)pentyl, 6-[1H-tetrazol-5-yl]hexyl, or the like, in which the preferred one may be tetrazolyl($C_1$-$C_6$) alkyl and the more preferred one may be (1H-tetrazol-5-yl)methyl, 2-(1H-tetrazol-5-yl)ethyl, 3-(1H-tetrazol-5-yl)propyl, 4-(1H-tetrazol-5-yl)butyl, 5-(1H-tetrazol-5-yl)pentyl and 6 (1H-tetrazol-5-yl)hexyl.

Suitable "tetrazolyl(higher)alkyl" may be 7-(1H-tetrazol-5-yl)heptyl, 8-(1H-tetrazol-5-yl)octyl, 4-(1H-tetrazol-1-yl)octyl, 8-(1H-tetrazol-5-yl)-3-methylheptyl, 9-(1H-tetrazol-5-yl)nonyl, 1-(1H-tetrazol-1-yl)nonyl, 10-(1H-tetrazol-5-yl)decyl, 8-(1H-tetrazol-5-yl)undecyl, 12-(1H-tetrazol-5-yl)dodecyl, 11-(1H-tetrazol-5-yl)-4-methylundecyl, 13-(1H-tetrazol-5-yl)tridecyl, 6-(1H-tetrazol-5-yl)tetradecyl, 15-(1H-tetrazol-5-yl)pentadecyl, 12-(1H-tetrazol-5-yl)hexadecyl, 17-(1H-tetrazol-1-yl)heptadecyl, 4-[1H-tetrazol-5-yl)octadecyl, 19-(1H-tetrazol-5-yl)nonadecyl, 1-(1H-tetrazol-1-yl)-12-ethylheptadecyl, 20-(1H-tetrazol-5-yl)icosyl, or the like, in which the preferred one may be tetrazolyl($C_7$-$C_{16}$)alkyl and the more preferred one may be 7-(1H-tetrazol-5-yl)heptyl, 8-(1H-tetrazol-5-yl)octyl, 9-(1H-tetrazol-5-yl)nonyl, 10-(1H-tetrazol-5-yl)decyl and 12-(1H-tetrazol-5-yl)dodecyl.

Suitable "lower al m in "lower alkyl having a group of the formula $$-N\bigcirc$$

can be referred to the ones as exemplified before for "carboxy(lower)alkyl"

Suitable "carboxy[lower)alkyl" can be referred to the ones as exemplified before for "carboxy(lower)alkyl" moiety of "carboxy(lower)alkylamino(lower)alkyl".

Suitable "protected carboxy(lower)alkyl" can be referred to the ones as exemplified before for "protected carboxy(lower)alkyl" moiety of "protected carboxy(lower)alkylamino(lower)alkyl".

Suitable "lower alkyl having hydroxy and aryloxy" may include 1-(1-naphthyloxy)-1-hydroxymethyl, 1-hydroxy-2-phenoxyethyl, 2-hydroxy-3-(1-naphthyloxy)propyl, 4-hydroxy-3-(p-tolyloxy)butyl, 4-hydroxy-1-(2-naphthyloxy)butyl, 1-hydroxy-5-(1-naphthyloxy)pentyl, 2-hydroxy-4-(2-naphthyloxy)hexyl, and the like.

Suitable "lower alkylamino having hydroxy and aryloxy" may include 1-(1-naphthyloxy)-1-hydroxymethylamino, 1-hydroxy-2-phenoxyethylamino, 2-hydroxy-3-(1-naphthyloxy)propylamino, 4-hydroxy-3-(p-tolyloxy)butylamino, 4-hydroxy-1-(2-naphthyloxy)butylamino, 1-hydroxy-5-(1-naphthyloxy)pentylamino, 2-hydroxy-4-(2-naphthyloxy)hexylamino, and the like.

Suitable "hydroxy(lower)alkyl" can be referred to the ones as exemplified before.

Suitable "lower alkyl having epoxy and aryloxy" may include 1,2-epoxy-2-(1-naphthyloxy)ethyl, 1,2-epoxy-3-(1-naphthyloxy)propyl, 3,4-epoxy-3-(p-tolyloxy)butyl, 1,2-epoxy-5-(1-naphthyloxy)pentyl, 2,3-epoxy-4-(2naphthyloxy)hexyl, and the like.

Suitable "lower alkylamino" can be referred to the ones as exemplified before for "lower alkylamino" moiety of "lower alkylamino(lower)alkyl".

Suitable "carboxy(lower)alkylamino" can be referred to the ones as exemplified before for "carboxy(lower)alkylamino" moiety of "carboxy(lower)alkylamino(lower)alkyl".

Suitable "protected carboxy(lower)alkylamino" can be referred to the ones as exemplified before for "protected carboxy(lower)alkylamino" moiety of "protected carboxy(lower)alkylamino(lower)alkyl".

Suitable "protected amino" can be referred to the ones as exemplified before for "acylamino".

Suitable "halogen" may include fluoro, chloro, bromo and iodo.

Suitable "halo(lower)alkyl" may include bromomethyl, 1-chloroethyl, 2-fluoroethyl, 3-iodopropyl, 2-bromobutyl, 4-chlorobutyl, 2-bromo-1,1-dimethylethyl, 4-bromopentyl, 5-bromopentyl, 6-bromohexyl, and the like, in which the preferred one may be halo($C_3$-$C_6$)alkyl Suitable "halo(higher)alkyl" may include 7-bromoheptyl, 8-bromooctyl, 4-chlorooctyl, 8-fluoro-3-methylheptyl, 9-bromononyl, 1-iodononyl, 10-bromodecyl, 8-chloroundecyl, 12-bromododecyl, 11-fluoro-4-methylundecyl, 13-chlorotridecyl, 6-bromotetradecyl, 15-bromopentadecyl, 12-chlorohexadecyl, 17-fluoroheptadecyl, 4-bromooctadecyl, 19-iodononadecyl, 1-fluoro-12-ethylheptadecyl, 20-bromoicosyl, and the like, in which the preferred one may be halo($C_7$-$C_{16}$)alkyl.

Suitable "arylsulfonyl" may include phenylsulfonyl, tolylsulfonyl, naphthylsulfonyl and the like, and said "arylsulfonyl" may have one or more (preferably 1 to 3) suitable substituent(s) such as aforesaid lower alkoxy, aforesaid halogen, or the like.

Suitable "a leaving group" may include di(lower)alkylamino (e.g. dimethylamino, diethylamino, N-ethylpropylamino, dibutylamino, N-pentylhexylamino, etc.), tri(lower)alkylammonio (e.g. trimethylammonio, etc.), lower alkoxy as mentioned above, halogen as mentioned above, lower alkylthio (e.g. methylthio, ethylthio, propylthio, butylthio, pentylthio, hexylthio, etc.), acyloxy such as lower alkanoyloxy (e.g. acetoxy, etc.), sulfonyloxy like lower alkyl sulfonyloxy (e.g. mesyloxy, etc.), arylsulfonyloxy (e.g. phenylsulfonyloxy, tosyloxy, etc.), or the like, and the like.

Suitable "anion" may be formate, acetate, trifluoroacetate, maleate, tartrate, methanesulfonate, benzenesulfonate, toluenesulfonate, chloride, bromide, iodide, sulfate, phosphate, or the like.

The processes for preparing the object compounds of the present invention are explained in detail in the following.

PROCESS 1

The compound (I) or a salt thereof can be prepared by reacting the compound (II) or a salt thereof with the compound (III) or a salt thereof.

Suitable salt of the compound (II) can be referred to an acid addition salt as exemplified for the compound (I).

Suitable salt of the compound (III) can be referred to the ones as exemplified for the compound (I).

The present reaction may be carried out in a solvent such as water, phosphate buffer, acetone, chloroform, acetonitrile nitrobenzene, methylene, chloride, ethylene chloride, formamide, N,N-dimethylformamide, methanol, ethanol, sec-butanol, amyl alcohol, diethyl ether, dioxane, tetrahydrofuran, dimethyl sulfoxide, or any other organic solvent which does not adversely affect the reaction, preferably in ones having strong polarities. Among the solvents, hydrophilic solvents may be used in a mixture with water. When the compound (III) is in liquid, it can also be used as a solvent. The reaction is preferably conducted in the presence of a base, for example, inorganic base such as alkali metal hydroxide, alkali metal carbonate, alkali metal bicarbonate, alkali metal hydride, organic base such as trialkylamine, and the like.

The reaction temperature is not critical, and the reaction is usually carried out at ambient temperature, under warming or under heating.

The present reaction is preferably carried out in the presence of alkali metal halide [e.g. sodium iodide, potassium iodide, etc.], alkali metal thiocyanate [e.g. sodium thiocyanate, potassium thiocyanate, etc.]or the like.

PROCESS 2

The compound (Ib) or a salt thereof can be prepared by subjecting the compound (Ia) or a salt thereof to elimination reaction of amino protective group.

Suitable salts of the compounds (Ia) and (Ib) can be referred to acid addition salts as exemplified for the compound (I).

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], hydrazine, picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.]and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.]or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.]or metallic compound [e.g. chromium chloride, chromium acetate, etc.]and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g.

reduced copper, Raney copper, Ullman copper, etc.-]and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof. The reaction temperature of this reduction is not critical and the reaction is usually carried out under cooling to warming.

PROCESS 3

The compound (Ic) or a salt thereof can be prepared by reacting the compound (Ib) or a salt thereof with the compound (IV) or a salt thereof.

Suitable salts of the compounds (Ic) and (IV) can be referred to the ones as exemplified for the compound (I).

This reaction can be carried out in a similar manner to that of Process 1 mentioned in the above, and therefore the reaction mode and reaction conditions [e.g. base, acid, catalyst, solvent, reaction temperature, etc.]of this reaction are to be referred to those as explained in Process 1.

PROCESS 4

The compound (Ie) or a salt thereof can be prepared by subjecting the compound (Id) or a salt thereof to elimination reaction of carboxy protective group.

Suitable salt of the compound (Id) can be referred to acid addition salt as exemplified for the compound (I).

Suitable salt of the compound (Ie) can be referred to the ones as exemplified for the compound (I).

This reaction can be carried out in a hydrolysis condition of Process 2 mentioned in the above, and therefore the reaction mode and reaction conditions [e.g. base, acid, catalyst, solvent, reaction temperature, etc.]of this reaction are to be referred to those as explained in Process 2.

PROCESS 5

The compound (If) or a salt thereof can be prepared by reacting the compound (Ib) or a salt thereof with the compound (V).

Suitable salt of the compound (If) can be referred to an acid addition salt as exemplified for the compound (I).

This reaction can be carried out in a similar manner to that of Process 1 mentioned in the above, and therefore the reaction mode and reaction conditions [e.g. base acid, catalyst, solvent, reaction temperature, etc.]of this reaction are to be referred to those as explained in Process 1.

PROCESS 6

The compound (Ig) or a salt thereof can be prepared by reacting the compound (VI) or its reactive derivative at hydroxy group or a salt thereof with the compound (VII) or a salt thereof.

Suitable reactive derivative at hydroxy group of the compound (VI) may be the derivative obtained by reacting the compound (VI) with thionyl halide (e.g. thionyl chloride, etc.), phosphoryl halide (e.g. phosphoryl chloride, etc.), sulfonyl halide (e.g. tosyl chloride, mesyl chloride, etc.), or the like.

Suitable salt of the compound [VI] can be referred to an acid addition salt as exemplified for the compound (I).

Suitable salts of the compounds (Ig) and (VII) can be referred to the ones as exemplified for the compound (I).

This reaction can be carried out in a similar manner to that of Process 1 mentioned in the above, and therefore the reaction mode and reaction conditions [e.g. base, acid, catalysts, solvent, reaction temperature, etc.]or this reaction are to be referred to those as explained in Process 1.

PROCESS 7

The compound (Ii) or a salt thereof can be prepared by subjecting the compound (Ih) or a salt thereof to formation reaction of tetrazolyl group.

Suitable salts of the compounds (Ih) and (Ii) can be referred to acid addition salts as exemplified for the compound (I).

The formation reaction of tetrazolyl group of this step can be carried out by reacting the compound (Ih) or a salt thereof with an azido compound such as alkali metal azide (e.g. sodium azide, etc.) or the like.

The reaction is usually carried out in a solvent such as N-methylpyrrolidone, toluene, dimethyl sulfoxide, acetone, or any other solvent which does not adversely influence the reaction.

The reaction can be carried out in the presence of a base such as tri(lower)alkylamine (e.g. trimethylamine, triethylamine, etc.) or the like.

The reaction temperature is not critical and the reaction can be carried out under warming or heating.

PROCESS 8

The compound (Ij) or a salt thereof can be prepared by subjecting the compound (VI) or a salt thereof to dehydration reaction.

Suitable salt of the compound (Ij) can be referred to an acid addition salt as exemplified for the compound (I).

The reaction can be carried out by the method disclosed in Example mentioned later or a similar manner thereto.

PROCESS 9

The compound (Ih) or a salt thereof can be prepared by subjecting the compound (VIII) or a salt thereof to cyanation reaction.

The suitable salt of the compound (VIII) can be referred to acid addition salts as exemplified for the compound (I).

The cyanation reaction of this step can be carried out by reacting the compound (VIII) or a salt thereof with alkali metal cyanide (e.g. sodium cyanide, etc.).

The reaction can be carried out in a similar manner to that of Process 1 mentioned in the above, and therefore the reaction mode and reaction conditions of this reaction are to be referred to those as explained in Process 1.

The processes for preparing the starting compound (II) or a salt thereof are explained in detail in the following.

PROCESS A

Step 1 to 3

The reactions of these steps can be carried out by the methods disclosed in Preparations mentioned later or the similar manners thereto.

Step 4

The compound (XVI) or a salt thereof can be prepared by reacting the compound (XIV) or a salt thereof with the compound (XV).

Suitable salts of the compounds (XIV) and (XVI) can be referred to acid addition salts as exemplified for the compound (I).

The reaction is usually carried out in a solvent such as water, methylene chloride, ethylene chloride, N,N-dimethylformamide or any other solvent which does not adversely influence the reaction or a mixture thereof.

The reaction can be carried out in the presence of a base such as alkali metal hydroxide (e.g. sodium hydroxide, potassium hydroxide, etc.), ar(lower)alkyltri(lower)alkylammonium halide (e.g. benzyltrimethylammonium chloride, etc.) or the like.

The reaction temperature is not critical and the reaction is usually carried out under cooling, at room temperature or under warming.

Step 5

The compound (II) or a salt thereof can be prepared by subjecting the compound (XVI) or a salt thereof to hydrolysis.

Suitable salt of the compound (XVI) can be referred to an acid addition salt as exemplified for the compound (I).

This reaction can be carried out in a hydrolysis condition of Process 2 mentioned in the above, and therefore the reaction mode and reaction conditions [e.g. base, acid, catalyst, solvent, reaction temperature, etc.]of this reaction are to be referred to those as explained in Process 2.

In order to show the usefulness of the compound (I) of the present invention, the pharmacological test result of the representative compound of the present invention is shown in the following.

TEST 1: ACTIVITY OF INCREASING THE RENAL BLOOD FLOW

[I] Test Method

Adult Beagle dogs of either sex, weighing were used. Under anesthesia with pentobarbital sodium (35 mg/kg i.p.), the trachea was intubated for artificial respiration. Catheters were placed in an femoral vein for drug administration.

A short segment of left renal artery was exposed by a flank incision and cleared of adhering tissue to accommodate positioning of an electromagnetic flow probe. Renal blood flow was measured by connecting the flow probe to an flowmeter.

[II]Test Compound

3-[2-(2-Dimethylaminoethyl)-3-oxo-2,3-dihydropyridazin-6-yl]-2-phenylpyrazolo[1,5-a]pyridine hydrochloride

[III] Result

| Dose (mg/kg) | Increasing % of Renal Blood Flow |
| --- | --- |
| 0.32 | +26.0 |

TEST 2: TEST ON DIURETIC ACTIVITY

[I] Test Method

Male JCL:SD strain rats aged 6 weeks and weighing about 200 g were used after starving for 18 hours. Immediately after oral dosing with the test compound suspended in 0.5% methylcellulose (0.5% MC), the animals werè given 20 ml/kg physiological saline orally. The rats were housed by threes in a metabolism cage. The urine was collected for 6 hours. Urinary electrolyte ($Na^+$) was measured with a Stat/Ion ® System (Technichon). The tests were conducted in 3 groups of 3 animals each.

[II]Test Compound

3-[2-{3-(1H-Tetrazol-5-yl)propyl}-3-oxo-2,3-dihydropyridazin-6-yl]-2-phenylpyrazolo[1,5-a]pyridine

[III]Test Result

The urine volume and urinary electrolyte [($Na^+$) [%, control=100%) were as follows.

| Dose (mg/kg) | Urine Volume (%) | $Na^+$ (%) |
| --- | --- | --- |
| 10.0 | 250 | 316 |

TEST 3: TEST ON ADENOSINE ANTAGONISM

[I]Test Method

Male Hartley strain guinea-pigs, weighing 500–650 g, were killed by bleeding and the hearts were removed.

An atrial strip was removed and suspended in an organ bath containing 50 ml of Tyrode's solution maintained at 27°–30° C. and aerated with a gas mixture of 95% $O_2$—5% $CO_2$. The atrium was connected to a strain gauge under an initial tension of 0.4–0.6 g. After constant motility had been obtained, the test compound and the adenosine ($1 \times 10^{-5}M$) were added. The negative inotropic activity of the adenosine was compared in the absence or presence of the test compound and then the adenosine antagonistic activities were measured.

[II]Test Compound

The same compound as used in Test 2

[III]Test Result

The negative inotropic activity of the adenosine was as follows.

| | Inhibiton (%) |
| --- | --- |
| In the absence of Test Compound | 70.4 ± 4.1 |
| In the presence of | 1.0 ±-0.6** |

-continued

| Test Compound (dose: 1 × 10⁻⁸ M) | Inhibiton (%) |

(mean ± S.E.)
**P <0.01 (vs absence of Test Compound)

TEST 4: TEST ON PROTECTIVE EFFECT IN GLYCEROL-INDUCED renal toxicity in rats

[I]Test Method

Male Sprague-Dawley rats (weighing 290–310 g) were fasted and dehydrated for 24 hours, renal toxicity was produced by intramuscular injection of 25% V/V glycerol in sterile saline (0.9% W/V NaCl), 10 ml/kg body weight. One hour before the injection of glycerol, rats were given a single oral dose of either test compound [1 mg/kg] or vehicle (5 ml/kg of 0.5% methyl cellulose). Twenty-four hours after glycerol injection, each rat was anesthetized with ether and blood sample was taken from abdominal aorta for the determination of plasma creatinine and BUN (blood urine nitrogen).

[II]Test Compound

The same compound as used in Test 2

[III]Test Result

| Group | BUN (mg/dl) (mean ± S.E.) | Plasma creatinine (mg/dl) (mean ± S.E.) |
|---|---|---|
| vehicle | 63.6 ± 10.2 | 2.15 ± 0.34 |
| Test Compound (1 mg/kg) | 29.2** ± 5.9 | 1.09** ± 0.10 |

**P <0.01

The pharmaceutical composition of this invention can be used in the form of a pharmaceutical preparation, for example, in solid, semisolid or liquid form, which contains the pyrazolopyridine compound (I) or a pharmaceutically acceptable salt thereof, as an active ingredient in admixture with an organic or inorganic carrier or excipient suitable for rectal, pulmonary [nasal or buccal inhalation), nasal, ocular, external (topical), oral or parenteral (including subcutaneous, intravenous and intramuscular) administrations or insufflation. The active ingredient may be compounded, for example, with the usual non toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The pyrazolopyridine compound (I) or a pharmaceutical acceptable salt thereof is/are included in the pharmaceutical composition in an amount sufficient to produce the desired aforesaid pharmaceutical effect upon the process or condition of diseases.

For applying the composition to human being or animals, it is preferable to apply it by intravenous, intramuscular, pulmonary, or oral administration, or insufflation. While the dosage of therapeutically effective amount of the pyrazolopyridine compound (I) varies from and also depends upon the age and condition of each individual patient to be treated, in the case of intravenous administration, a daily dose of 0.01–100 mg of the pyrazolopyridine compound (I) per kg weight of human being or animals, in the case of intramuscular administration, a daily dose of 0.1–100 mg of the pyrazolopyridine compound (I) per kg weight of human being or animals, in case of oral administration, a daily dose of 0.5–100 mg of the pyrazolopyridine compound (I) per kg weight of human being or animals is generally given for th prevention and/or treatment of aforesaid diseases.

The following Preparations and Examples are given for the purpose of illustrating the present invention in more detail.

PREPARATION 1

A mixture of 3,6-dichloropyridazine (50 g), sodium benzenesulfinate dihydrate (100 g), benzyltrimethylammonium chloride (62.3 g), and 1,4-dioxane (335 ml) was stirred for 3 hours at 100° C. After being cooled to room temperature, aqueous solution of sodium hydroxide (510 ml) was added to the mixture, and the mixture was stirred for 0.5 hour at 100° C. The reaction mixture was cooled in a water bath and acidified with 36% hydrochloric acid (35 ml). The precipitate formed was collected, washed well with water, and dried to give 6-phenylsulfonyl-3-oxo-2,3-dihyiropyridazine (54.7 g).

mp : 189°–191° C.

IR (Nujol) : 1680, 1650, 1370, 1160 cm$^{-1}$

NMR (DMSO-d$_6$, δ) : 7.12 (1H, d, J=10Hz), 7.6–7.9 (3H, m), 7.9–8.1 (3H, m) 13.85 (1H, broad s)

MASS m/z: 236

Anal. Calcd. for $C_{10}H_8N_2O_3S$: C 50.84, H 3.41, N 11.86, S 13.57 (T);

Found : C 51.10, H 3.33, N 11.70, S 13.23 (%)

PREPARATION 2

To stirring phosphorous oxychloride (87 ml) at 80° C. was added four 2.0 g portions of 6-phenylsulfonyl-3-oxo-2,3-dihydropyridazine every 30 minutes. After additional two 1.0 g portions were added with stirring, the reaction mixture was slowly poured into ice-water over 1 hour to form the precipitate, which was collected, washed well with water, and dried to give 6-chloro-3-ph-enylsulfonylpyridazine (8.4 g).

An analytical sample was prepared by recrystallization from a mixture of diisopropyl ether and acetone (3:1).

mp : 142°–144° C.

IR (Nujol 3100, 3050, 1580, 1540, 1370, 1180 cm$^{-1}$

NMR (CDCl$_3$, δ) : 7.5–7.7 (3H, m), 7.74 (1H, d, J=9Hz), 8.0–8.2 (2H, m), 8.25 (1H, d, J=9Hz) MASS m/z: 192 (M+· 62), 190 (M+· 64), 155 Anal. Calcd. for $C_{10}H_7ClN_2O_2S$: C 47.16, H 2.77, N 11.00, S 12.59 (%);

Found: C 47.09, H 2.65, N 10.71, S 12.12 (%)

PREPARATION 3

To a solution of 6-chloro-3-phenylsulfonylpyridazine (8.4 g) bis(triphenylphosphine)palladium(II) chloride (98%; 0.24 g), copper(I) iodide (95%; 63 mg), and triethylamine (9.2 ml) in N,N-dimethylformamide (84 ml) was added phenylacetylene (4.7 ml), and the mixture was stirred for 0.5 hour at 80° C. After being cooled to room temperature, water (168 ml) was added to the reaction mixture. The precipitate formed was collected, washed with water, and dried. Recrystallization of the crude product from a mixture of diisopropyl ether and acetone (2:1) gave 6-(2-phenylethynyl)-3-phenylsulfonylpyridazine (5.5 g). After the mother liquor was concentrated in vacuo, the residue was triturated with acetone. The precipitate was collected and dried to give a second crop of the pure material (2.0 g).

mp: 179°-181° C.

IR (Nujol): 2200, 1370, 1180 cm$^{-1}$

NMR (CDCl$_3$, δ): 7.3-7.5 (3H, m), 7.5-7.7 (5H, m), 7.81 (1H, d, J=9Hz), 8.1-8.2 (2H, m), 8.25 (1H, d, J=9Hz)

MASS m/z: 256 (M$^+$- 64)

Anal. Calcd. for C$_{18}$H$_{12}$N$_2$O$_2$S: C 67.48, H 3.78, N 8.74, S 10.00 (%);

Found : C 67.53, H 3.69, N 8.23, S 9.71 (%),

PREPARATION 4

A two-phase mixture of 6-(2-phenylethynyl)-3-phenylsulfonylpyridazine (23.3 g), 1-aminopyridinium iodide (90%; 26.9 g), sodium hydroxide (11.6 g), and benzyltrimethylammonium chloride (1.35 g) in a mixture of methylene chloride (233 ml) and water (233 ml) was stirred for 2 hours at room temperature. Water (233 ml) was added to the reaction mixture, and the mixture was acidified with 36% hydrochloric acid (20 ml). The organic layer was separated, washed twice with water and once with sodium chloride aqueous solution, dried over anhydrous magnesium sulfate, and concentrated. The residue was washed with hot ethanol (300 ml) to give 3-(3-phenylsulfonylpyridazin-6-yl)-2-phenylpyrazolo[1,5-a]pyridine (20.8 g). An analytical sample was prepared by recrystallization from ethyl acetate.

mp : 192°-194° C.

IR (Nujol): 1620, 1560, 1370, 1180 cm$^{-1}$

NMR (CDCl$_3$, δ): 6.9-7.1 (1H, m), 7.3-7.5 (1H, m), 7.36 (1H, d, J=9Hz), 7.5-7.9 (8H, m), 7.93 (1H, d, J=9Hz), 8.1-8.2 (2H, m), 8.5-8.6 (2H, m)

MASS m/z: 412, 411 (M$^+$- 1)

Anal. Calcd. for C$_{23}$H$_{16}$N$_4$O$_2$S: C 66.98, H 3.91, N 13.58, S 7.77 (%), Found: C 67.31, H 3.83, N 13.34, S 7.95 (%),

PREPARATION 5

A mixture of 3-(3-phenylsulfonylpyridazin-6-yl)-2-phenylpyrazolo[1,5-a]pyridine (20.0 g), sodium hydroxide solution (80 ml; containing 7.8 g of sodium hydroxide), and 1,4-dioxane (40 ml) was stirred for 2 hours under reflux. After being cooled to room temperature, the reaction mixture was acidified with 36% hydrochloric acid (15 ml). The precipitate formed was collected, washed with three 25 ml portions of water, and dried to give 3-(3-oxo-2,3-dihydropyridazin-6-yl)-2-phenylpyrazolo[1,5-a]pyridine (16.0 g). An analytical sample was prepared by recrystallization from ethyl acetate.

mp : 229°-230° C.

IR (Nujol): 1680, 1630 cm$^{-1}$

NMR (DSM 6): 6.84 [1H, d, J=10Hz), 7.12 (1H, d, J=10Hz), 7.0-7.1 (1H, m), 7.3-7.7 (6H, m), 7.86 (1H, broad d, J=9Hz), 8.82 (1H, broad d, J=7Hz), 13.19 (1H, broad s)

MASS m/z: 288, 287 (M$^+$- 1)

Anal. Calcd. for C$_{17}$H$_{12}$N$_4$O C 70.82, H 4.20, N 19.43 (%);

Found : C 70.93, H 4.18, N 19.38 (%),

PREPARATION 6

To an ice-cooled solution of 3-(3-oxo-2,3-dihydropyridazin-6-yl)-2-phenylpyrazolo[1,5-a]pyridine (2.0 g) in N,N-dimethylformamide (20 ml) was added portionwise sodium hydride (60% dispersion in mineral oil; 0.31 g). After addition was finished, the mixture was stirred for 15 minutes in an ice-bath. To this mixture was added 4-chlorobutyl acetate (1.1 g), and the reaction mixture was stirred for 24 hours at room temperature, and then for 36 hours at 70° C. After being cooled to room temperature, the reaction mixture was concentrated. The residue was partitioned between ethyl acetate and water.

The organic layer was separated and the aqueous layer was extracted twice with ethyl acetate. The combined organic layers were washed with water and sodium chloride aqueous solution, dried over anhydrous magnesium sulfate, and concentrated. Purification of the residue by column chromatography on silica gel (using 3:1 mixture of chloroform and ethyl acetate as eluent) gave 3-[2-(4-acetoxybutyl)-3-oxo-2,3-dihydropyridazin-6-yl]2-phenylpyrazolo[1,5-a]pyridine (2.6 g). An analytical sample was prepared by recrystallization from diisopropyl ether.

mp 102°-103° C.

IR (Nujol): 1720, 1660 cm$^{-1}$

NMR (CDCl$_3$, δ): 1.7-1.9 (2H, m), 1.9-2.2 (2H, m), 2.05 (3H, s), 4.16 (2H, t-like, J=ca. 6Hz), 4.31 (2H, t-like, J=ca. 6Hz), 6.77 (1H, d, J=10Hz), 6.8-7.0 (1H, m), 7.02 (1H, d, J=10Hz), 7.2-7.4 (1H, m), 7.4-7.5 (3H, m), 7.6-7.7 (2H, m), 7.9-8.0 (1H, m), 8.5-8.6 (1H, m)

MASS m/z: 402, 343, 287

Anal. Calcd. for C$_{23}$H$_{22}$N$_4$O$_3$: C 68.64, H 5.51, N 13.92 (%);

Found : C 68.31, H 5.48, N 13.76 (%).

PREPARATION 7

To an ice-cooled solution of 3-[2-(4-acetoxybutyl)-3-oxo-2,3-dihydropyridazin-6-yl]-2-phenylpyrazolo[1,5-a]pyridine (2.6 g) in methanol (18 ml) was added a solution of sodium hydroxide (0.78 g) in methanol (8 ml). After addition was finished, the mixture was stirred for 15 minutes at room temperature. The reaction mixture was concentrated, and the residue was diluted with chloroform and water. The organic layer was separated and the aqueous layer was extracted twice with chloroform. The combined organic layers were washed with sodium chloride aqueous solution, dried over anhydrous magnesium sulfate, and concentrated.

Purification of the residue by column chromatography on silica gel (using a mixture of chloroform and methanol (25:1) as an eluent) gave 3-[2-(4-hydroxybutyl)-3-oxo-2,3-dihyiropyridazin-6-yl]-2-phenylpyrazolo[1,5-a]pyridine (1.8 g). An analytical sample was prepared by recrystallization from toluene.

mp : 115°-116° C.

IR (Nujol): 3400, 1660, 1630 cm$^{-1}$

NMR (CDCl$_3$, δ): 1.6-1.8 (2H, m), 1.9-2.1 (2H, m), 2.41 (1H, broad s), 3.74 (2H, broad t), 4.32 (2H, t-like, J=ca. 7Hz), 6.76 (1H, d, J=9Hz), 6.7-7.0 (1H, m), 7.01 (1H, d, J=9Hz), 7.2-7.4 (1H, m), 7.4-7.5 (3H, m), 7.5-7.7 (2H, m), 7.9-8.0 (1H, m), 8.5-8.6 (1H, m)

MASS m/z: 289, 287 (M$^+$-73)

Anal. Calcd. for C$_{21}$H$_{20}$N$_4$O$_2$: C 69.98, H 5.59, N 15.55 (%); Found: C 70.25, H 5.56, N 15.43 (%),

PREPARATION 8

To a suspension of 3-(3-oxo-2,3-dihydropyridazin-6-yl)-2-phenylpyrazolo[1,5-a]pyridine (1.0 g) and sodium hydride (60% 0.15 g) in N,N-dimethylformamide (10 ml) was added acetoxyethyl bromide (0.58 g) at 5° C., and the resulting mixture was stirred at room temperature for 18 hours. The reaction mixture was poured into ice-water, and extracted twice with ethyl acetate. The extracts were combined, washed successively with 1N sodium hydroxide solution and sodium chloride aqueous solution, dried over magnesium sulfate, and then evaporated in vacuo. The residue was dissolved in 1,4-dioxane (12 ml) and a solution of sodium hydroxide (0.34 g) in water (1.5 ml) was added thereto. The reaction mixture was stirred at 60° C. for 3 hours, and evaporated in vacuo. The residue was treated with water and extracted with chloroform. The extract was washed with sodium chloride aqueous solution, dried over magnesium sulfate, and then evaporated in vacuo. The residue was crystallized from ethyl acetate to afford 3-[2-(2-hydroxyethyl)-3-oxo-2,3-dihydropyridazin-yl]-2-phenylpyrazolo[1,5-a]pyridine (0.84 g).

mp: 185.5°-187° C.

IR (Nujol): 3350, 1650, 1580, 1520, 1500 cm$^{-1}$

NMR (CDCl$_3$, δ): 4.05 (2H, m), 4.30 (2H, d, J=4Hz), 6.70 (1H, d, J=10Hz), 6.82 (1H, td, J=7Hz and 1Hz), 7.00 (1H, d, J=10Hz), 7.15-7.60 [6H, m), 7.87 (1H, d, J=10Hz), 8.45 (1H, d, J=7Hz)

MASS : 332 (M+)

Analysis Calcd. for C$_{19}$H$_{16}$N$_4$O$_2$: C 68.66, H 4.85, N 16.86 (%);

Found : C 67.29, H 5.05, N 16.42 (%),

EXAMPLE 1

To a suspension of 3-(3-oxo-2,3-dihydropyridazin-6-yl)-2-phenylpyrazolo[1,5-a]pyridine (1.00 g) and sodium hydride (0.37 g, 60%) in N,N-dimethylformamide (5 ml) was added 4-(2-chloroethyl)morpholine hydrochloride (0.98 g). After being stirred for 1.5 hours at 70° C., the reaction mixture was poured into water (100 ml), and extracted twice with methylene chloride.

The combined extracts were washed with water, dried over anhydrous sodium sulfate and evaporated in vacuo. The residue was treated with a 20% solution of hydrogen chloride in ethanol (2 ml) to afford 3-[2-(2-morpholinoethyl)-3-oxo-2,3-dihydropyridazin-6-yl]-phenylpyrazolo[1,5-a]pyridine hydrochloride (0.72 g).

mp : 231.5°-233° C.

IR (Nujol): 2325, 1670, 1590 cm$^{-1}$

NMR (CDCl$_3$, δ): 3.18 (2H, m), 3.56 (4H, m), 3.75-4.0 (4H, m), 4.57 (2H, m), 6.93 [1H, d, J=10Hz), 7.13 (1H, t, J=6Hz), 7.14 (1H, d, J=10Hz), 7.40-7.68 (6H, m), 8.05 (1H, d, J=8Hz), 8.93 (1H, d, J=7Hz), 11.04 (1H, broad s)

MASS : 401 (M+)

The following compounds (Examples 2 to 12) were obtained according to a similar manner to that of Example 1.

EXAMPLE 2

3-[2-(2-Piperidinoethyl)-3-oxo-2,3-dihydropyridazin-6-yl]-2-phenylpyrazolo[1,5-a]pyridine hydrochloride mp : 262.5°-265° C.

IR (Nujol): 2495, 1660, 1595 cm$^{-1}$

NMR (DMSO-d$_6$, δ): 1.78 (6H, m), 2.99 (2H, m), 3.45 (4H, m), 4.56 (2H, m), 6.95 (1H, d, J=9Hz), 7.07 (1H, t, J=17Hz), 7.15 (1H, d, J=9Hz), 7.40-7.65 (6H, m), 8.04 (1H, d, J=9Hz), 8.84 (1H, d, J=7Hz), 9.80 (1H, broad s)

MASS : 399 (M+)

EXAMPLE 3

3-[2-(2-Dimethylaminoethyl)-3-oxo-2,3-dihydropyridazin-6-yl]-2-phenylpyrazolo[1,5-a]pyridine hydrochloride mp: 148.5°-149.5° C.

IR (Nujol): 3520, 3450, 2600, 2370, 1640, 1570 cm$^{-1}$

NMR (CDCl$_3$, δ): 2.92 (6H, s), 3.53 (2H, m), 4.77 (2H, m), 6.76 (1H, d, J=10Hz), 6.95 (1H, t, J=6Hz), 7.09 (1H, d, J=10Hz), 7.37-7.64 (6H, m), 8.15 (1H, d, J=8Hz), 8.53 (1H, d, J=7Hz), 13.10 (1H, broad s)

EXAMPLE 4

3-[2-(3-Dimethylaminopropyl)-3-oxo-2,3-dihydropyridazin-6-yl]-2-phenylpyrazolo[1,5-a]pyridine hydrochloride mp: 248°-249° C.

IR (Nujol): 2400, 1655, 1590 cm$^{-1}$

NMR (DMSO-d$_6$, δ): 2.15 (2H, m), 2.18 (2H, m), 2.75 (6H, s), 4.22 (2H, t, J=7Hz), 7.10 (1H, d, J=10Hz), 7.12 (1H, t, J=7Hz), 7.13 (1H, d, J=10Hz), 7.42-7.63 (6H, m), 7.99 (1H, d, J=12Hz), 8.83 (1H, d, J=8Hz), 10.1 (1H, broad s)

EXAMPLE 5

3-[2-(2-Phthalimidoethyl)-3-oxo-2,3-dihydropyridazin-yl]-2-phenylpyrazolo[1,5-a]pyridine mp: 180°-181° C. (recrystallized from ethanol)

IR (Nujol): 1760, 1710, 1660, 1630 cm$^{-1}$

NMR (CDCl$_3$, δ): 4.1-4.3 (2H, m), 4.5-4.6 (2H, m), 6.70 (1H, d, J=10Hz), 6.8-6.9 (1H, m), 6.91 (1H, d, J=10Hz), 7.0-7.1 (1H, m), 7.3-7.7 (10H, m), 8.3-8.4 (1H, m)

MASS m/z: 461, 301, 287

Anal. Calcd. for C$_{27}$H$_{19}$N$_5$O$_3$: C 70.27, H 4.15, N 15.18 (%); Found : C 70.35, H 4.20, N 15.18 (%),

EXAMPLE 6

3-[2-(2-Cyanoethyl)-3-oxo-2,3-dihydropyridazin-6-yl]-2-ph-enylpyrazolo[1,5-a]pyridine mp 170°-170.5° C.

IR (Nujol): 1660, 1580 cm$^{-1}$

NMR (CDCl$_3$, δ): 3.00 (2H, t, J=7Hz), 4.55 (2H, t, J=7Hz), 6.77 (1H, d, J=10Hz), 6.94 (1H, t, J=6Hz), 7.06 (1H, d, J=10Hz), 7.26-7.63 (6H, m), 8.14 (1H, d, J=9Hz), 8.53 (1H, d, J=6Hz)

Anal. Calcd. : C 70.36, H 4.43, N 20.52 (%);

Found: C 70.49, H 4.41, N 20.62 (%),

EXAMPLE 7

3-[2-(3-Cyanopropyl)-3-oxo-2,3-dihydropyridazin-6yl]-2-phenylpyrazolo[1,5-a]pyridine mp: 100°-102° C.

IR (Nujol): 1655, 1580 cm$^{-1}$

NMR (CDCl$_3$, δ): 2.2-2.4 2H, m), 2.51 (2H, t, J=6.9Hz), 4.40 (2H, t, J=6.6Hz), 6.77 [(1H, d, J=9.7Hz), 6.94 (1H, td, J=6.9Hz and J=1.3Hz), 7.06 (1H, d, J=9.7Hz), 7.3-7.7 (6H, m), 8.01 (1H, d, J=9.0Hz), 8.54 (1H, d, J=7.0Hz)

MASS: 355

EXAMPLE 8

3-[2-(4-Cyanobutyl)-3-oxo-2,3-dihydropyridazin-6-yl]-phenylpyrazolo[1,5-a]pyridine mp: 140°-142° C.

IR (Nujol): 1655, 1590 cm$^{-1}$

NMR (DMSO-d$_6$, δ): 1.5-1.75 (2H, m), 1.8-2.0 (2H, m), 2.5 (2H, t, J=7.0Hz), 4.18 (2H, t, J=6.8Hz), 6.88 (1H, d, J=9.6Hz), 7.0-7.15 (2H, m), 7.35-7.65 (6H, m), 7.95 (1H, d, J=8.9Hz), 8.82 (1H, d, J=6.9Hz)

EXAMPLE 9

3-(2-Benzyl-3-oxo-2,3-dihydropyridazin-6-yl)-2phenylpyrazolo[1,5-a]pyridine mp 182.5°-183.5° C.

IR (Nujol): 1670, 1640, 1600, 1530 cm$^{-1}$

NMR (CDCl$_3$, δ): 5.45 (2H, s), 6.76-7.63 (15H, m), 8.50 (1H, d, J=8Hz)

MASS : 378 (M+)
Anal. Calcd. : C 76.17, H 4.79, N 14.80 (%);
Found C 76.44, H 4.84, N 14.78 (%).

EXAMPLE 10

3-[2-(2-Oxo-1,3-oxazolidin-5-yl)methyl-3-oxo-2,3-dihyropyridazin-6-yl]-2-phenylpyrazolo[1,5-a]pyridine mp: 165.5°–166° C.

IR (Nujol): 3350–3400, 1715, 1690, 1645, 1580, 1520, 1495 cm$^{-1}$

NMR (CDCl$_3$, δ): 3.28 (1H, q, J=6Hz), 3.49 (1H, m), 4.24 (1H, m), 4.44 (2H, d, J=5Hz), 5.45 (1H, broad s), 6.80 (1H, d, J=10Hz), 6.91 (1H, t, J=6Hz), 6.95 (1H, d, J=10Hz), 7.26–7.62 (6H, m), 8.00 (1H, d, J=10Hz), 8.54 (1H, d, J=7Hz)

MASS: 387 (M+)

Anal. Calcd. for C$_{21}$H$_{17}$N$_5$O$_3$: C 62.22, H 4.69, N 17.28 (%); Found : C 62.94, H 4.91, N 16.65 (%),

EXAMPLE 11

3-[2-(4-Pyridylmethyl)-3-oxo-2,3-dihydropyridazin-yl]-2-phenylpyrazolo[1,5-a]pyridine mp: 165.5°–166° C.

IR (Nujol): 1670, 1630, 1590, 1560, 1530 cm$^{-1}$

NMR (CDCl$_3$, δ): 5.44 (2H, s , 6.80 (1H, d, J=10Hz), 6.90 (1H, t, J=6Hz), 7.05 (1H, d, J=10Hz), 7.19–7.68 (9H, m), 8.51 (1H, d, J=8Hz), 8.64 (2H, s)

MASS: 379 (M+)

Anal. Calcd. : C 72.81, H 4.52, N 18.46 (%); Found C 73.19, H 4.57, N 18.54 (%),

EXAMPLE 12

3-(2-Tetrahydro-2H-pyran-2-yl)-3-oxo-2,3-dihydropyridazin-6-yl)-2-phenylpyrazolo[1,5-a]pyridine mp: 165°14 165.5° C.

IR (Nujol): 1660, 1630, 1590, 1530 cm$^{-1}$

NMR (CDCl$_3$, δ): 1.52–1.88 (6H, m), 3.44 (1H, t, J=11Hz), 4.01 (2H, t, J=11Hz), 4.31 (2H, d, J=6Hz), 6.77 (1H, d, J=10Hz), 6.90 (1H, t, J=6Hz), 6.95 (1H, d, J=10Hz), 7.26–7.66 (6H, m), 8.11 (1H, d, J=10Hz), 8.52 (1H, d, J=6Hz)

MASS: 386 (M+)

Anal. Calcd. for C$_{23}$H$_{22}$N$_3$O$_2$: C 71.48, H 5.47, N 14.50 (%);
Found: C 71.26, H 5.67, N 14.45 (%).

EXAMPLE 13

A mixture of 3-[2-(2-phthalimidoethyl)-3-oxo-2,3-dihydropyridazin-6-yl]-2-phenylpyrazolo[1,5-a]pyridine (2.2 g), hydrazine monohydrate (2 ml), and ethanol (100 ml) was stirred for 1 hour under reflux. After being cooled to room temperature, the reaction mixture was concentrated, and the residue was partitioned between chloroform and water. The organic layer was separated, and extracted with 10% hydrochloric acid. The aqueous layer was washed twice with chloroform, neutralized with sodium hydroxide, and extracted three times with chloroform. The combined organic layers were washed with water and sodium chloride aqueous solution, dried over anhydrous magnesium sulfate, and concentrated to give 3-[2-(2-aminoethyl)-3-oxo-2,3-dihydropyridazin-6-yl]-2-phenylpyrazolo[1,5-a]pyridine (1.5 g). An analytical sample was prepared by recrystallization from ethyl acetate.

mp: >142° C.

IR (Nujol): 3380, 3300, 1660, 1630 cm$^{-1}$

NMR (CDCl$_3$, δ): 1.47 (2H, broad s), 3.25 (2H, t-like, J=ca. 6Hz), 4.35 (2H, t-like, J=ca. 6Hz), 6.78 (1H, d, J=10Hz), 6.9–7.0 (1H, m), 7.04 (1H, d, J=10Hz), 7.3–7.4 (1H, m), 7.4–7.5 (3H, m), 7.6–7.7 (2H, m), 7.9–8.0 (1H, m), 8.5–8.6 (1H, m)

MASS m/z: 331, 302

EXAMPLE 14

To an ice-cooled solution of 3-[2-(2-aminoethyl)-3-oxo-2,3-dihydropyridazin-6-yl]-2-phenylpyrazolo[1,5-a]pyridine (1.5 g), triethylamine (1.5 ml), and N,N-dimethylformamide (15 ml) was added ethyl 2-bromoacetate (0.60 ml), and the mixture was stirred for 1 hour at room temperature. The reaction mixture was concentrated, and the residue was partitioned between chloroform and water. The organic layer was separated, washed with sodium chloride aqueous solution, dried over anhydrous magnesium sulfate, and concentrated.

Purification of the residue by column chromatography on silica gel (gradient elution, using 50:1 and 25:1 mixture of chloroform and methanol) gave 3-[2-{2-(ethoxycarbonylmethylamino)ethyl}-3-oxo-2,3-dihydropyridazin-6-yl]-2-phenylpyrazolo[1,5-a]pyridine (0.90 g).

mp: 212°–214° C.

IR (Nujol): 2750, 2170, 2120, 2430, 1760, 1650, 1630 cm$^{-1}$

NMR (CDCl$_3$, δ) 1.24 (3H, t, J=7Hz), 3.72 (2H, broad t, J=ca. 5Hz), 4.04 (2H, s), 4.21 (2H, q, J=7Hz), 4.79 (2H, broad t, J=ca. 5Hz , 6.79 (1H, d, J=10Hz), 6.8–6.9 (1H, m), 7.05 (1H, d, J=10Hz), 7.3–7.5 (4H, m), 7.6–7.7 (2H, m), 8.0–8.1 (1H, m), 8.4–8.5 (1H, m), 9.2–11.0 (1H, broad m)

MASS m/z: 417, 344, 315, 302

EXAMPLE 15

To a solution of 3-[2-{2- ethoxycarbonylmethylamino)ethyl}-3-oxo-2,3-dihydropyridazin-6-yl]-2-phenylpyrazolo1,5-a]pyridine 0.80 g) in ethanol (8 ml) was added a solution of sodium hydroxide (0.15 g) in water (4 ml) and the mixture was stirred for 0.5 hour at room temperature. The reaction mixture was concentrated and the residue was partitioned between water and ethyl acetate. The aqueous layer was separated, neutralized with 1N hydrochloric acid to give the precipitate, which was collected and purified by recrystallization from 50% aqueous ethanol to give 3-[2-(2-(carboxyethylamino)ethyl}-3-oxo-2,3-dihydro-pyridazin-6-yl]-2-phenylpyrazolo[1,5-a]pyridine (0.50 g).

mp: 230°–232° C.

IR (Nujol): 3400, 1650, 1600 cm$^{-1}$

NMR (CDCl$_3$-CD$_3$OD=1:1, δ): 3.19 (2H, broad t, J=ca. 6Hz , 3.22 (2H, s), 4.30 (2H, broad t, J=ca. 6Hz , 6.54 (1H, d, J=10Hz), 6.7–6.8 (1H, m), 6.83 (1H, d, J=10Hz), 7.1–7.2 (4H, m), 7 2–7.4 (2H, m), 7.7–7.8 (1H, m), 8.2–8.3 (1H, m)

EXAMPLE 16

A mixture of 3-[2-(2-aminoethyl)-3-oxo-2,3-dihydropyridazin-6-yl]-2-phenylpyrazolo[1,5-a]pyridine (0.50 g), 1-[(2,3-epoxypropyl)oxy]naphthalene (0.36 g), and 1,4-dioxane (15 ml)-water (1.5 (ml) was stirred for 1 hour at 50° C., and then for 2 hours under reflux.

After being cooled to room temperature, the reaction mixture was concentrated, and the residue was purified by column chromatography on silica gel (gradient elution, using 50:1 and 25:1 mixture of chloroform and methanol) to give 3-[2-{2-{2-hydroxy-3-(1-naphthyloxy)propylamino-}ethyl}-3-oxo-2,3-dihydropyridazin-6-yl]-2-phenylpyrazolo[1,5-a]pyridine (0.49 g).

NMR (CDCl$_3$, δ) 2.0–3.0 (2H, broad m), 2.9–3.1 (2H, m), 3.1–3.4 (2H, m), 4.0–4.3 (3H, m), 4.3–4.6 (2H, m), 6.7–6.8 (2H, m), 6.8–6.9 (1H, m), 6.98 (1H, d, J=10Hz), 7.0–7.5 (8H, m), 7.5–7.6 (2H, m), 7.7–7.8 (1H, m), 7.9–8.0 (1H, m), 8.1–8.2 (1H, m), 8.4–8.5 (1H, m)

MASS m/z: 532 (M$^+$ + 1)

EXAMPLE 17

3-[2-{2-{2-Hydroxy-3-(1-naphthyloxy)-propylamino}ethyl}-3-oxo-2,3-dihydropyridazin-6-yl]-2-phenylpyrazolo1,5-a]pyridine hydrochloride was obtained according to a conventional manner from the compound obtained in Example 16.

IR (Nujol): 3300 (br), 1650, 1630 cm$^{-1}$

NMR (DMSO-d6, δ): 3.2–3.6 (4H, m), 4.1–4.2 (2H, m), 4.3–4.7 (1H, broad m), 4.59 (2H, broad m), 6.10 (1H) broad m), 6.94 (1H, d, J=10Hz), 6.9–7.0 (1H, m), 7.0–7.2 (1H, m), 7.13 (1H, d, J=10Hz), 7.3–7.6 (8H, m), 7.6–7.7 (2H, m), 7.8–7.9 (1H, m), 8.0–8.1 (1H, m), 8.2–8.3 (1H, m), 8.8–9.0 (1H, m), 9.0–9.3 (1H, broad m), 9.3–9.7 (1H, broad m)

EXAMPLE 18

To an ice-cooled solution of 3-[2-(4-hydroxybutyl)-3-oxo-2,3-dihydropyridazin-6-yl]-2-phenylpyrazolo[1,5-a]pyridine (1.5 g) in methylene chloride (15 ml) was added thionyl chloride (0.37 ml), and the solution was stirred for 0.5 hour at room temperature. Additional thionyl chloride (0.37 ml) was added to the mixture, and stirring was continued for 1 hour at room temperature followed by 1 hour at 40° C. Again, additional thionyl chloride (0.37 ml) was added, and the mixture was stirred for 1 hour under reflux. After being cooled to room temperature, the reaction mixture was concentrated to give the intermediate chloride compound.

To a solution of this intermediate chloride compound in sec-butyl alcohol (15 ml) was added 50% aqueous solution of dimethylamine (10 ml), and the mixture was stirred for 6 hours under reflux. After being cooled to room temperature, the reaction mixture was concentrated. The residue was dissolved in 1N hydrochloric acid and washed with ethyl acetate. The aqueous layer was separated, neutralized with sodium hydroxide, and extracted three times with chloroform. The combined organic layers were washed with saturated aqueous solution of sodium bicarbonate and sodium chloride aqueous solution, dried over anhydrous magnesium sulfate, and concentrated. Purification of the residue by column chromatography on silica gel (gradient elution, using 10:1 and 5:1 mixture of chloroform and methanol) gave 3-[2-(4-dimethylaminobutyl)-3-oxo-2,3-dihydropyridazin-6-yl]-2-ohenylpyrazolo[1,5-a]pyridine This amine was dissolved in ethanol (5 ml) and treated with 20% solution of hydrogen chloride in ethanol (5 ml). The mixture was concentrated, and the residue was purified by recrystallization from a mixture of ethanol and diisopropyl ether to give 3-[2-(4-dimethylaminobutyl)-3-oxo-2,3-dihydropyridazin-6-yl]-2-phenylpyrazolo[1,5-a]pyridine hydrochloride (0.89 g).

mp: 215° to 216° C.

IR (Nujol): 3100, 3050, 2400, 1660, 1630 cm$^{-1}$

NMR (DMSO-d$_6$, δ): 1.6–2.0 (4H, broad m), 2.70 (6H, s), 3.08 (2H, broad s), 3.40 (1H, broad s), 4.1–4.2 (2H, broad m), 6.89 (1H, d, J=10Hz), 7.0–7.1 (1H, m), 7.10 (1H, d, J=10Hz), 7.4–7.5 (4H, m), 7.5–7.7 (2H, m), 7.97 (1H, m), 8.83 (1H, m)

MASS m/z: 387, 329

EXAMPLE 19

A solution of 3-[2-(2-hydroxyethyl)-3-oxo-2,3-dihydropyridazin-6-yl]-2-phenylpyrazolo[1,5-a]pyridine (0.5 g) and thionyl chloride (0.13 ml) in methylene chloride (4 ml) was stirred at room temperature for 1 hour and evaporated in vacuo. To the residue was added dropwise a solution of 1-(2-hydroxyethyl)piperazine (0.78 g) in amyl alcohol (5 ml), and the suspension was refluxed for 1.5 hours. The reaction mixture was evaporated in vacuo, and the residue was purified by column chromatography on silica gel using chloroform as eluent. The obtained oil was treated with a 20% solution of hydrogen chloride in ethanol to afford 3-[2-{2-{4-(2-}ethyl}-3-oxo-2,3-hydroxyethyl)piperazin-1-yl}ethyl}-3-oxo-2,3-dihydropyridazin-6-yl]-2-phenylpyrazolo[1,5-a]pyridine dihydrochloride.

mp: 240°–241.5° C.

IR (Nujol): 3400, 1660, 1590 cm$^{-1}$

NMR (DMSO-d$_6$, δ): 3.42–3.79 (17H, m), 4.51 (2H, broad s), 6.90 (1H, d, J=10Hz), 7.08 (1H, t, J=6Hz), 7.10 (1H, d, J=10Hz), 7.40–7.70 (6H, m), 8.06 (1H, d, J=9Hz), 8.83 (1H, d, J=6Hz)

Anal. Calcd.: C 55.25, H 6.08, N 15.47 (%);
Found C 55.16, H 6.32, N 15.18 (%),

EXAMPLE 20

3-[2-{2-{4-(2-Methoxyphenyl)piperazin-1-yl}ethyl}-3-oxo-2,3-dihydropyridazin-6-yl]-2-phenyl-pyrazolo[1,5-a]pyridine was obtained according to a similar manner to that of Example 19.

mp: 120°–125° C.

IR (Nujol) 1680, 1585, 1525, 1500 cm$^{-1}$

NMR (CDCl$_3$, δ) 2.84 (4H, m), 2.97 (2H, t, J=6Hz), 3.13 (4H, m), 3.87 (3H, s), 4.47 (2H, t, J=6Hz 6.76 (1H, d, J=10Hz), 6.85–7.65 (12H, m), 8.05 (1H, d, J=10Hz), 8.53 (1H, d, J=7Hz)

MASS: 506 (M$^+$- 1)

Anal. Calcd.: C 71.13, H 5.97, N 16.59 (%);
Found: C 71.17, H 5.96, N 16.58 (%).

EXAMPLE 21

A mixture of 3-[2-(2-cyanoethyl)-3-oxo-2,3-dihyiropyridazin-6-yl]-2-phenylpyrazolo[1,5-a]pyridine (0.35 g), sodium azide (0.20 g) and triethylamine hydrochloride (0.21 g) in N-methylpyrrolidone (10 ml) was stirred at 150° C. for 4 hours under nitrogen atmosphere. The reaction mixture was poured into water (30 ml), acidified with 10% hydrochloric acid (5 ml), and extracted twice with ethyl acetate. The combined extracts were washed with water, dried over magnesium sulfate and evaporated in vacuo. The residue was purified by column chromatography on silica gel using a mixture of chloroform and methanol (20:1) as an eluent. The fractions containing the object compound were combined and evaporated in vacuo. The residue was recrystallized from ethyl acetate to give 3-[2-{2-(1H-tetrazol-5-yl)ethyl}-3-oxo-2,3-dihydropyridazin-6-yl]-2-phenylpyrazolo[1,5-a]pyridine (0.06 g).

mp: 230°–232° C. (decomp.)

IR (Nujol): 1660, 1585 cm$^{-1}$

NMR (CDCl$_3$, δ) : 3.74 (2H, t, J=6Hz), 4.83 (2H, t, J=6Hz), 6.90 (1H, d, J=10Hz), 6.98 (1H, t, J=6Hz), 7.15 (1H, d, J=10Hz), 7.26–7.58 (6H, m), 7.96 (1H, d, J=7Hz), 8.56 (1H, d, J=6Hz), 11.96 (1H, broad s)

The following compounds (Examples 22 and 23) were obtained according to a similar manner to that of Example 21.

EXAMPLE 22

3-[2-{3-(1H-Tetrazol-5-yl)propyl}-3-oxo-2,3-dihydropyridazin-6-yl]-2-phenylpyrazolo[1,5-a]pyridine mp: 215°–217° C.

IR (Nujol): 1665, 1595 cm$^{-1}$

NMR (DMSO-d6, 6): 2.15–2.35 (2H, m), 3.00 (2H, t, J=7.6Hz), 4.26 (2H, t, J=6.9Hz), 6.86 (1H, d, J=9.7Hz), 7.05–7.15 (2H, m), 7.35–7.65 (6H, m), 7.96 (1H, d, J=8.9Hz), 8.82 (1H, d, J=6.9Hz)

MASS: 398, 355, 287

Anal. Calcd. for $C_{21}H_{18}N_8O$: 63.31, N 4.55, H 28.12 (%);

Found: C 63.03, N 4.53, H 27.98 (%).

EXAMPLE 23

3-[2-{4-(1H-Tetrazol-5-yl)butyl}-3-oxo-2,3-dihydropyridazin-6-yl]-2-phenylpyrazolo[1,5-a]pyridine mp: 213° to 214° C.

IR (Nujol): 1635, 1565 cm$^{-1}$

NMR (DMSO-d6, 6): 1.7–2.0 (4H, m), 2.97 (2H, t, J=6.7Hz), 4.19 (2H, m), 6.88 (1H, d, J=9.7Hz), 7.0–7.2 (2H, m), 7.35–7.5 (4H, m), 7.5–7.65 (2H, m), 7.89 (1H, d, J=8.9Hz), 8.82 (1H, d, J=6.9Hz)

EXAMPLE 24

A solution of 3-[2-(2-hydroxyethyl)-3-oxo-2,3-dihydropyridazin-6-yl]-2-phenylpyrazolo[1,5-a]pyridine (0.5 g) and thionyl chloride (0.13 ml) in methylene chloride (4 ml) was stirred at room temperature for 1 hour and then evaporated in vacuo. To the residue were added, Triton B (2.04 g) and methylene chloride (4 ml). The reaction mixture was refluxed for 2 hours, poured into water (10 ml) and extracted with chloroform. The extract was washed with water, dried over magnesium sulfate and evaporated in vacuo.

The residue was purified by column chromatography on silica gel using chloroform as an eluent. The obtained oil was crystallized from a mixture of ethanol and ethyl acetate (1:1) to afford 3-(2-vinyl-3-oxo-2,3-dihydropyridazin-6-yl)-2-phenylpyrazolo[1,5-a]pyridine.

mp: 187.5°–188° C.

IR (Nujol): 1680, 1635, 1605 cm$^{-1}$

NMR (CDCl$_3$, δ): 5.05 (1H, d, J=10Hz), 5.87 (1H, d, J=16Hz), 6.77 (1H, d, J=10Hz), 6.94–7.03 (2H, m), 7.26–7.66 (6H, m), 7.87 (1H, dd, J=16Hz and 10Hz), 8.10 (1H, d, J=10Hz), 8.55 (1H, d, J=7Hz)

Anal. Calcd.: C 72.60, H 4.49, N 17.83 (%);

Found C 72.85, H 4.62, N 18.00 (%).

EXAMPLE 25

A mixture of 3-(3-oxo-2,3-dihydropyridazin-6-yl)-2phenylpyrazolo[1,5-a]pyridine (0.60 g), 2,2-dimethyl-3,4-epoxy-6-cyano-3,4-dihydro-2H-chromene (0.80 g), and 60% sodium hydride (0.16 g) in dimethylsulfoxide (6 ml) was stirred for 5 hours at 60° C., and then diluted with ethyl acetate. The mixture was washed with water (10 ml) and sodium chloride aqueous solution (10 ml), dried over magnesium sulfate, and evaporated in vacuo. The residue was chromatographed on silica gel (10 g) with a mixture of n-hexane and ethyl acetate (2:1). The fractions containing the object compound were combined and evaporated in vacuo. The residue was recrystallized from a mixture of ethyl acetate and diisopropyl ether to give 3-[2-(2,2-dimethyl-3-hydroxy-6-cyano-3,4-dihydro-2H-chromen-4-yl)-3-oxo-2,3-dihydropyridazin-6-yl]-2phenylpyrazolo[1,5-a]pyridine (0.51 g).

mp: 209°–210° C.

IR (Nujol): 3330, 2220, 1670, 1600 cm$^{-1}$

NMR (CDCl$_3$, δ): 1.41 (3H, s), 1.56 (3H, s), 3.32 (1H, d, J=5.8Hz), 4.25 (1H, m), 6.35 (1H, d, J=9.0Hz), 6.3–7.2 (7H, m), 7.4–7.6 (6H, m), 8.45 (1H, d, J=6.9Hz)

MASS: 489 (M+), 456, 287

Anal. Calcd.: C 71.15, H 4.74, N 14.31 (%);

Found C 70.97, H 4.75, N 14.06 (%).

PREPARATION 9

Potassium iodide (0.1 g) and 1,5-dibromopentane (4.6 g) were added to a suspension of 3-(3-oxo-2,3-dihydropyridazin-6-yl)-2-phenylpyrazolo[1,5-a]pyridine (2.88 g) and 60% sodium hydride [0.4 g] in N,N-dimethylformamide (40 ml). After being stirred for 3 hours at room temperature, the mixture was poured into cold water and extracted with ethyl acetate. The extract was washed with water, dried over magnesium sulfate, and evaporated in vacuo. The oily residue was purified by column chromatography on silica gel (100 g) using chloroform as an eluent to afford 3-[2-(5-bromopentyl)-3-oxo-2,3-dihydropyridazin-6-yl]-2-phenylpyrazolo[1,5-a]pyridine (3.48 g).

mp: 111° to 112° C. (recrystallized from a mixture of diethyl ether and ethyl acetate)

IR (Nujol): 1660, 1650 (shoulder), 1625, 1580 cm$^{-1}$

NMR (CDCl$_3$, δ): Ca. 1.5–2.1 (6H, m), 3.44 (2H, t, J=6.7Hz), 4.29 (2H, t, J=7.2Hz), 6.77 (1H, d, J=9.6Hz), 6.92 (1H, t, J=6.9Hz), 7.02 (1H, d, J=9.6Hz), 7.33 (1H, t, J=6.8Hz), 7.42–7.64 (5H, m), 7.98 (1H, d, J=7.9Hz), 8.53 (1H, d, J=6.9Hz)

The following compounds (Preparations 10 to 15) were obtained according to a similar manner to that of Preparation 9.

PREPARATION 10

3-[2-(6-Bromohexyl)-3-oxo-2,3-dihydropyridazin-6-yl]-2-phenylpyrazolo[1,5-a]pyridine mp: 94° to 95° C.

IR (Nujol): 1655, 1630, 1590 cm$^{-1}$

NMR (CDCl$_3$, δ): Ca. 1.3–1.7 (4H, m), Ca. 1.7–2.1 (4H, m), 3.42 (2H, t, J=6.7Hz), 4.27 (2H, t, J=7.3Hz), 6.77 (1H, d, J=9.6Hz), 6.93 (1H, t, J=6.9Hz), 7.02 (1H, d, J=9.6Hz), 7.29–7.37 (1H, m), 7.44–7.47 (3H, m), 7.59–7.64 (2H, m), 7.97 (1H, d, J=8.9Hz), 8.55 (1H, d, J=6.9Hz)

PREPARATION 11

3-[2-(7-Bromoheptyl)-3-oxo-2,3-dihydropyridazin-2-phenylpyrazolo[1,5-a]pyridine

IR (Film/NaCl): 1655, 1630, 1585 cm$^{-1}$

NMR (CDCl$_3$, δ): Ca. 1.3–2.2 (10H, m), 3.41 (2H, t, J=6.8Hz), 4.27 (2H, t, J=7.4Hz), 6.76 (1H, d, J=9.6Hz), 6.92 (1H, t, J=6.9Hz), 7.01 (1H, d, J=9.6Hz), 7.32 (1H, t, J=6.8Hz), 7.42–7.64 (5H, m), 7.98 (1H, d, J=7.9Hz), 8.53 (1H, d, J=6.9Hz)

PREPARATION 12

3-[2-(8-Bromooctyl)-3-oxo-2,3-dihydropyridazin-6-yl]-phenylpyrazolo[1,5-a]pyridine mp: 84° to 85° C.

IR (Nujol): 1655, 1630, 1580 cm$^{-1}$

NMR (CDCl$_3$, δ): Ca. 1.2–1.7 (8H, broad), Ca. 1.7–2.1 (4H, m), 3.40 (2H, t, J=6.8Hz), 4.27 (2H, t, J=7.4Hz), 6.76 (1H, d, J=9.6Hz), 6.92 (1H, t, J=6.9Hz), 7.01 {(1H, d, J=9.6Hz), 7.27–7.35 (1H, m), 7.43–7.47 (3H, m), 7.58–7.64 (2H, m), 7.97 (1H, d, J=8.9Hz), 8.53 (1H, d, J=6.9Hz)

PREPARATION 13

3-[2-(9-Bromononyl)-3-oxo-2,3-dihydropyridazin-6-yl]-2-phenylpyrazolo[1,5-a]pyridine mp: 85° to 87° C.

IR (Nujol): 1650, 1625, 1580, 1520 cm$^{-1}$

NMR (CDCl$_3$, δ): 1.20–1.67 (10H, m), 1.67–2.20 (4H, m), 3.40 (2H, t, J=6.8Hz), 4.27 (2H, t, J=7.4Hz), 6.77 (1H, d, J=9.6Hz), 6.96 (1H, t, J=6.9Hz), 7.00 (1H, d, J=9.6Hz), 7.32 (1H, m), 7.40–7.50 (3H, m), 7.50–7.68 (2H, m), 7.98 (1H, d, J=8.9Hz), 8.55 (1H, d, J=7.0Hz)

PREPARATION 14

3-[2-(10-Bromodecyl)-3-oxo-2,3-dihydropyridazin-6yl]-2-phenylpyrazolo[1,5-a]pyridine mp: 59° to 60° C.

IR Nujol): 1650, 1625, 1585, 1520 cm$^{-1}$

NMR (CDCl$_3$, δ) : 1.20–1.57 (12H, m), 1.70–2.03 (4H, m), 3.40 (2H, t, J=6.8Hz), 4.27 (2H, t, J=7.4Hz), 6.76 (1H, d, J=9.6Hz), 6.92 (1H, t, J=6.9Hz), 7.00 (1H, d, J=9.6Hz), 7.31 (1H, m), 7.37–7.52 (3H, m), 7.53–7.68 (2H, m), 7.98 (1H, d, J=8.9Hz), 8.54 (1H, d, J=7.0Hz)

PREPARATION 15

3-[2-(12-Bromododecyl)-3-oxo-2,3-dihydropyridazin-6yl]-2-phenylpyrazolo[1,5-a]pyridine mp: 70° to 71° C.

IR (Nujol): 1655, 1630, 1590, 1525 cm$^{-1}$

NMR (CDCl$_3$, δ) : 1.13–1.53 (16H, m), 1.73–2.03 (4H, m), 3.40 (2H, t, J=6.8Hz), 4.27 (2H, t, J=7.4Hz), 6.76 (1H, d, J=9.6Hz), 6.92 (1H, t, J=6.9Hz), 7.00 (1H, d, J=9.6Hz), 7.31 (1H, m), 7.37–7.50 (3H, m), 7.55–7.67 (2H, m), 7.98 (1H, d, J=8.9Hz), 8.53 (1H, d, J=6.0Hz)

EXAMPLE 26

A mixture of 3-[2(5-bromopentyl)-3-oxo-2,3-pyridazin-6-yl]-2-phenylpyrazolo[1,5-a]pyridine (2.753 g) and sodium cyanide (0.37 g) in dimethyl sulfoxide (12.6 ml) was stirred at room temperature for 2 hours and then at 60° C. for 1 hour. To the mixture was added water and extracted with ethyl acetate. The extract was washed with water, dried over magnesium sulfate, and evaporated in vacuo. The residue was purified by column chromatography on silica gel using a mixture of chloroform and methanol as an eluent to afford 3-[2-(5-cyanopentyl)-3-oxo-2,3-dihydropyridazin-6-yl]-2-phenylpyrazolo[1,5-a]pyridine (1.75 g).

mp: 120.5° to 122° C. (recrystallized from ethyl acetate)

IR (Nujol): 2245 (weak), 1660, 1630 (shoulder), 1590 cm$^{-1}$

NMR (CDCl$_3$, δ): Ca. 1.5–2.1 (6H, m), 2.39 (2H, t, J=6.8Hz), 4.29 (2H, t, J=7.3Hz), 6.77 (1H, d, J=9.6Hz), 6.93 (1H, t, J=6.9Hz), 7.03 (1H, d, J=9.6Hz), 7.34 (1H, t, J=6.8Hz), 7.44–7.64 (5H, m), 7.96 (1H, d, J=7.8Hz), 8.54 (1H, d, J=7Hz)

The following compounds (Examples 27 to 32) were obtained according to a similar manner to that of Example 26.

EXAMPLE 27

3-[2-(6-Cyanohexyl)-3-oxo-2,3-dihydropyridazin-6yl]-2-phenylpyrazolo[1,5-a]pyridine mp: 85° to 87° C.

IR (Nujol): 2245 (weak), 1660, 1630, 1590 cm$^{-1}$

NMR (CDCl$_3$, δ) : Ca. 1.4–1.8 (6H, m), Ca. 1.8–2.1 (2H, m), 2.36 (2H, t, J=6.8Hz), 4.27 (2H, t, J=7.2Hz), 6.77 (1H, d, J=9.6Hz), 6.93 (1H, t, J=6.9Hz), 7.02 [(1H, d, J=9.6Hz), 7.29–7.38 (1H, m), 7.44–7.58 (3H, m), 7.59–7.64 (2H, m), 7.97 (1H, d, J=8.9Hz), 8.54 (1H, d, J=6.9Hz)

EXAMPLE 28

3-[2-(7-Cyanoheptyl)-3-oxo-2,3-dihydropyridazin-6yl]-2-phenylpyrazolo[1,5-a]pyridine mp: 112° to 113° C. (recrystallized from ethyl acetate)

IR (Nujol): 2250 (weak), 1660, 1630, 1590 cm$^{-1}$

NMR (CDCl$_3$, δ) : Ca. 1.4–2.1 (10H, m), 2.34 (2H, t, J=6.9Hz), 4.27 [2H, t, J=7.3Hz), 6.76 (1H, d, J=9.6Hz), 6.95 (1H, t, J=6.9Hz), 7.02 (1H, d, J=9.6Hz), 7.33 (1H, t, J=6.8Hz), 7.43–7.64 (5H, m), 7.98 (1H, d, J=8.9Hz), 8.53 (1H, d, J=7Hz)

EXAMPLE 29

3-[2-(8-Cyanooctyl)-3-oxo-2,3-dihydropyridazin-6yl]-2-phenylpyrazolo[1,5-a]pyridine mp: 94° to 96° C.

IR (Nujol): 2230 (weak), 1650, 1580 cm$^{-1}$

NMR (CDCl$_3$, δ) : Ca. 1.2–1.8 (10H, broad), Ca. 1.8–2.1 (2H, m), 1.89–1.92 (2H, m), 2.33 (2H, t, J=6.9Hz), 4.27 (2H, t, J=7.4Hz), 6.76 (1H, d, J=9.6Hz), 6.92 (1H, t, J=6.9Hz), 7.01 (1H, d, J=9.6Hz), 7.27–7.36 (1H, m), 7.44–7.58 (3H, m), 7.58–7.64 (2H, m), 7.98 (1H, d, J=8.9Hz), 8.53 (1H, d, J=6.9Hz)

EXAMPLE 30

3-[2-(9-Cyanononyl)-3-oxo-2,3-dihydropyridazin-6yl]-2-phenylpyrazolo[1,5-a]pyridine mp: 123° to 125° C.

IR (Nujol): 2240, 1655, 1630, 1585, 1525 cm$^{-1}$

NMR (CDCl$_3$, δ) : 1.20–1.53 (10H, m), 1.53–1.73 (2H, m), 1.80–2.03 (2H, m), 2.33 [2H, t, J=7.0Hz), 4.27 (2H, t, J=7.4Hz), 6.76 (1H, d, J=9.6Hz), 6.92 (1H, t, J=7.2Hz), 7.01 (1H, d, J=9.6Hz), 7.32 (1H, m), 7.40–7.55 (3H, m), 7.55–7.77 (2H, m), 7.98 (1H, d, J=8.9Hz), 8.54 (1H, d, J=6.9Hz)

EXAMPLE 31

3-[2-(10-Cyanodecyl)-3-oxo-2,3-dihydropyridazin-6yl]-2-phenylpyrazolo[1,5-a]pyridine mp: 77° to 79° C.

IR (Nujol): 2240, 1645, 1580, 1520 cm$^{-1}$

NMR (CDCl$_3$, δ) : 1.20–1.53 (12H, m), 1.53–1.75 (2H, m), 1.75–2.05 (2H, m), 2.33 (2H, t, J=7.0Hz), 4.27 (2H, t, J=7.4Hz), 6.76 (1H, d, J=9.6Hz), 6.92 (1H, t, J=6.9Hz), 7.00 (1H, d, J=9.6Hz), 7.31 (1H, m), 7.37–7.53 (3H, m), 7.53–7.70 (2H, m), 7.98 (1H, d, J=8.9Hz), 8.53 (1H, d, J=6.9Hz)

EXAMPLE 32

3-[2-(12-Cyanododecyl)-3-oxo-2,3-dihydropyridazin-6yl]-2-phenylpyrazolo[1,5-a]pyridine mp: 69° to 70° C.

IR (Nujol): 2240, 1655, 1630, 1585, 1530 cm$^{-1}$

NMR (CDCl$_3$, δ) : 1.20–1.55 (16H, m), 1.55–1.73 (2H, m), 1.83–2.03 (2H, m), 2.33 (2H, t, J=7.0Hz), 4.27 (2H, t, J=7.4Hz), 6.76 (1H, d, J=9.6Hz), 6.91 (1H, t, J=6.9Hz), 7.00 (1H, d, J=9.6Hz), 7.31 (1H, m), 7.37–7.50 (3H, m), 7.53–7.68 (2H, m), 7.98 (1H, d, J=8.9Hz), 8.53 (1H, d, J=6.9Hz)

EXAMPLE 33

3-[2-Cyanomethyl-3-oxo-2,3-dihydropyridazin-6-yl]-2phenylpyrazolo[1,5-a]pyridine was obtained according to a similar manner to that of Example 1.

mp: 218°–219° C.

IR (Nujol): 1670, 1660 (shoulder), 1625, 1590 cm$^{-1}$

NMR (CDCl$_3$, δ) : 5.18 (2H, s), 6.78 (1H, d, J=9.8Hz), 6.97 (1H, t, J=6.9Hz), 7.05 (1H, d, J=9.8Hz), 7.39 (1H, t, J=8Hz), 7.46–7.63 (5H, m), 8.15 (1H, d, J=9Hz), 8.55 (1H, d, J=6.9Hz)

The following compounds (Examples 34 to 41) were obtained according to a similar manner to that of Example 21.

EXAMPLE 34

3-[2-{(1H-Tetrazol-5-yl)methyl}-3-oxo-2,3-dihydro-pyridazin-6-yl]-2-phenylpyrazolo[1,5-a]pyridine mp: 252° to 254° C. (decomp.), (recrystallized from a mixture of chloroform and methanol)

IR (Nujol): 1650, 1580 cm$^{-1}$

NMR (DMSO-d$_6$, δ)): 5.72 (2H, s , 6.97 (1H, d, J=9.7Hz), 7.07 (1H, t, J=6.8Hz), 7.11 (1H, d, J=9.7Hz , 7.40 (1H, t, J=6.8Hz), 7.47–7.66 (5H, m), 7.83 (1H, d, J=8.9Hz), 8.82 (1H, d, J=6.9Hz)

EXAMPLE 35

3-[2-{5-(1H-Tetrazol-5-yl)pentyl}-3-oxo-2,3-dihydro-pyridazin-6-yl]-2-phenylpyrazolo[1,5-a]pyridine mp: 167° to 168° C. (recrystallized from a mixture of methanol and ethyl acetate)

IR (Nujol): 1635, 1560 cm$^{-1}$

NMR (DMSO-d$_6$, δ): Ca. 1.3–1.5 (2H, m), Ca. 1.7–1.9 (4H, m), 2.90 (2H, t, J=7.4Hz), 4.14 (2H, t, J=7.1Hz), 6.87 (1H, d, J=9.6Hz), Ca. 7.1 (1H, m), 7.10 (1H, d, J=9.6Hz), Ca. 7.4–7.7 (6H, m), 7.92 (1H, d, J=8.9Hz), 8.83 (1H, d, J=6.9Hz)

EXAMPLE 36

3-[2-{6-(1H-Tetrazol-5-yl)hexyl}-3-oxo-2,3-dihydro-pyridazin-6-yl]-2-phenylpyrazolo[1,5-a]pyridine mp: 183° to 185° C. (recrystallized from ethanol)

IR (Nujol): 1640, 1560 cm$^{-1}$

NMR (CDCl$_3$, δ) : Ca. 1.3–1.7 (4H, broad), Ca. 1.7–2.1 (4H, m), 3.03 (2H, t, J=7.(1Hz), 4.31 (2H, t, J=7.0Hz), 6.87 (1H, d, J=9.6Hz), 6.95 (1H, t, J=6.9Hz), 7.12 (1H, d, J=9.6Hz), 7.32–7.39 (1H, m), 7.45–7.48 (3H, m), 7.58–7.63 (2H, m), 7.99 (1H, d, J=8.9Hz), 8.55 (1H, d, J=6.9Hz)

EXAMPLE 37

3-[2-{7-(1H-Tetrazol-5-yl)heptyl}-3-oxo-2,3-dihydro-pyridazin-6-yl]-2-phenylpyrazolo[1,5-a]pyridine mp: 189.5° to 190.5° C. (recrystallized from a mixture of methanol and ethyl acetate)

IR (Nujol): 1650, 1580 cm$^{-1}$

NMR (DMS 6): Ca. 1.2–1.9 (10H, m), 2.87 (2H, t, J=7.5Hz), 4.13 (2H, t, J=7.(1Hz), 6.87 (1H, d, J=9.6Hz), Ca. 7.1 (1H, m), 7.11 (1H, d, J=9.6Hz), Ca. 7.4–7.7 (6H, m), 7.91 (1H, d, J=8.9Hz), 8.82 (1H, d, J=6.9Hz)

EXAMPLE 38

3-[2-{8-(1H-Tetrazol-5-yl)octyl)-3-oxo-2,3-dihydro-pyridazin-6-yl]-2-phenylpyrazolo[1,5-a]pyridine mp: 165° to 167° C. (recrystallized from ethanol)

IR (Nujol): 1635, 1550–1565 (broad) cm$^{-1}$

NMR (CDCl$_3$, Ca. 1.3–1.6 8H, broad), Ca. 1.7–2.1 (4H, m), 3.00 (2H, t, J=7.6Hz), 4.34 (2H, t, J=7.2Hz), 6.90 (1H, d, J=9.6Hz), 6.95 (1H, t, J=6.9Hz), 7.11 (1H, d, J=9.6Hz), 7.35 (1H, t, J=7.9Hz), 7.44–7.48 (3H, m), 7.58–7.63 (2H, m), 8.00 (1H, d, J=8.9Hz), 8.55 (1H, d, J=6.9Hz)

EXAMPLE 39

3-[2-{9-(1H-Tetrazol-5-yl)nonyl}-3-oxo-2,3-dihydro-pyridazin-6-yl]-2-phenylpyrazolo[1,5-a]pyridine mp: 155° to 156° C.

IR (Nujol): 1635, 1560, 1535, 1490 cm$^{-1}$

NMR (CDCl$_3$, δ) 1.13–1.60 (10H, m), 1.65–2.07 (4H, m), 2.99 (2H, t, J=7.8Hz), 4.34 (2H, t, J=7.5Hz), 6.95 (1H, m), 6.96 (1H, d, J=9.6Hz), 7.13 (1H, d, J=9.6Hz), 7.35 (1H, m), 7.43–7.53 (3H, m), 7.53–7.68 (2H, m), 8.00 (1H, d, J=8.9Hz), 8 55 {(1H, d, J=7.0Hz , 15.9 (1H, broad s)

EXAMPLE 40

3-[2-{10-(1H-Tetrazol-5-yl)decyl}-3-oxo-2,3-dihydro-pyridazin-6-yl]-2-phenylpyrazolo[1,5-a]pyridine mp: 135° to 136° C.

IR (Nujol): 1635, 1560, 1535, 1490 cm$^{-1}$

NMR (CDCl$_6$, δ): 1.13–1.57 (12H, m), 1.67–2.07 (4H, m), 2.97 (2H, t, J=7.6Hz), 4.33 (2H, t, J=7.4 Hz), 6.94 (1H, d, J=9.6Hz), 6.98 (1H, m), 7.11 (1H, d, J=9.6Hz), 7.35 (1H, m), 7.40–7.52 (3H, m), 7.52–7.67 (2H, m), 8.00 (1H, d, J=8.9Hz), 8.56 (1H, d, J=7.0Hz)

EXAMPLE 41

3-[2-{12-(1H-Tetrazol-5-yl)dodecyl}-3-oxo-2,3-dihydropyridazin-6-yl]-2-phenylpyrazolo[1,5-a]pyridine mp: 134°–to 135° C.

IR (Nujol 1635, 1560, 1535, 1490 cm$^{-1}$

NMR (CDCl$_3$, δ) : 1.10–1.55 (6H, m), 1.73–2.10 {(4H, m), 2.96 (2H, t, J=7.5Hz), 4.33 (2H, t, J=7.3Hz), 6.91 (1H, d, J=9.6Hz), 6.96 (1H, m), 7.09 (1H, d, J=9.6Hz), 7.35 (1H, m), 7.40–7.53 (3H, m), 7.53–7.70 (2H, m), 8.00 (1H, d, J=8.9Hz), 8.57 (1H, d, J=7.0Hz)

The following compounds (Examples 42 to 67) were obtained according to a similar manner to that of Example 1.

EXAMPLE 42

3-[2-(2-Aminoethyl)-3-oxo-2,3-dihyiropyridazin-6-yl]-phenylpyrazolo[1,5-a]pyridine IR (Nujol): 3380, 3300, 1660, 1630 cm$^{-1}$

EXAMPLE 43

3-[2-{2-(Ethoxycarbonylmethylamino)ethyl}-3-oxo-2,3-dihydropyridazin-6-yl]-2-phenylpyrazolo[1,5-a]pyridine IR (Nujol): 2750, 2170, 2120, 2430, 1760, 1650, 1630 cm$^{-1}$

EXAMPLE 44

3-[2-{2-(Carboxymethylamino)ethyl}-3-oxo-2,3-dihydro-pyridazin-6-yl]-2-phenylpyrazolo[1,5-a]pyridine IR (Nujol): 3400, 1650, 1600 cm$^{-1}$

EXAMPLE 45

3-[2-{2-{2-Hydroxy-3- 1 naphthyloxy)-propylamino}ethyl}-3-oxo-2,3-dihydropyridazin-6-yl]-2-phenylpyrazolo[1,5-a]pyridine NMR (CDCl$_3$, δ) : 2.0–3.0 2H, broad m), 2.9–3.1 (2H, m), 3.1–3.4 (2H, m), 4.0–4.3 (3H, m), 4.3–4.6 2H, m), 6.7–6.8 (2H, m), 6.8–6.9 (1H, m), 6.98 (1H, d, J=10Hz), 7.0–7.5 8H, m), 7.5–7 6 2H, m), 7.7–7.8 (1H, m), 7.9–8.0 (1H, m), 8.1–8.2 (1H, m), 8.4–8.5 (1H, m)

EXAMPLE 46

3-[2-(4-Dimethylaminobutyl)-3-oxo-2,3-dihydropyridazin-6-yl]-2-phenylpyrazolo[1,5-a]pyridine hydrochloride
IR (Nujol): 3100, 3050, 2400, 1660, 1630 cm$^{-1}$

EXAMPLE 47

3-[2-{2-{4-(2-Hydroxyethyl)piperazin-1-yl}ethyl}-3-oxo-2,3-dihydropyridazin-6-yl]-2-phenylpyrazolo[1,5-a]pyridine dihydrochloride
IR (Nujol): 3400, 1660, 1590 cm$^{-1}$

EXAMPLE 48

3-[2-{2-{4-(2-Methoxyphenyl)piperazin-1-yl}ethyl}-3-oxo-2,3-dihydropyridazin-6-yl]-2-phenylpyrazolo[1,5-a]-pyridine
IR (Nujol 1680, 1585, 1525, 1500 cm$^{-1}$

EXAMPLE 49

3-[2-{2-(1H-Tetrazol-5-yl)ethyl}-3-oxo-2,3-dihydropyridazin-6-yl]-2-phenylpyrazolo[1,5-a]pyridine
IR (Nujol 1660, 1585 cm$^{-1}$

EXAMPLE 50

3-[2-{3-(1H-Tetrazol-5-yl)propyl}-3-oxo-2,3-dihydropyridazin-6-yl]-2-phenylpyrazolo[1,5-a]pyridine
IR (Nujol): 1665, 1595 cm$^{-1}$

EXAMPLE 51

3-[2-{4-(1H-Tetrazol-5-yl)butyl}-3-oxo-2,3-dihydropyridazin-6-yl]-2-phenylpyrazolo[1,5-a]pyridine
IR (Nujol): 1635, 1565 cm$^{-1}$

EXAMPLE 52

3-(2-Vinyl-3-oxo-2,3-dihydropyridazin-6-yl)-2-phenylpyrazolo[1,5-a]pyridine
IR (Nujol): 1680, 1635, 1605 cm$^{-1}$

EXAMPLE 53

3-[2-[5-Cyanopentyl)-3-oxo-2,3-dihydropyridazin-6-yl]-2-phenylpyrazolo[1,5-a]pyridine
IR (Nujol): 2245 (weak), 1660, 1630 (shoulder), 1590 cm$^{-1}$

EXAMPLE 54

3-[2-(6-Cyanohexyl)-3-oxo-2,3-dihydropyridazin-6yl]-2-phenylpyrazolo[1,5-a]pyridine
IR (Nujol): 2245 (weak), 1660, 1630, 1590 cm$^{-1}$

EXAMPLE 55

3-[2-(7-Cyanoheptyl)-3-oxo-2,3-dihydropyridazin-6yl]-2-phenylpyrazolo[1,5-a]pyridine
IR (Nujol): 2250 (weak), 1660, 1630, 1590 cm$^{-1}$

EXAMPLE 56

3-[2-(8-Cyanooctyl)-3-oxo-2,3-dihydropyridazin-6-yl]-phenylpyrazolo[1,5-a]pyridine
IR (Nujol): 2230 (weak), 1650, 1580 cm$^{-1}$

EXAMPLE 57

3-[2-(9-Cyanononyl)-3-oxo-2,3-dihydropyridazin-6-yl]-2-phenylpyrazolo[1,5-a]pyridine
IR (Nujol): 2240, 1655, 1630, 1585, 1525 cm$^{-1}$

EXAMPLE 58

3-[2-(10-Cyanodecyl)-3-oxo-2,3-dihydropyridazin-6-yl]-2-phenylpyrazolo[1,5-a]pyridine
IR (Nujol): 2240, 1645, 1580, 1520 cm$^{-1}$

EXAMPLE 59

3-[2-(12-Cyanododecyl)-3-oxo-2,3-dihydropyridazin-6-yl]-2-phenylpyrazolo[1,5-a]pyridine
IR (Nujol): 2240, 1655, 1630, 1585, 1530 cm$^{-1}$

EXAMPLE 60

3-[2-{(1H-Tetrazol-5-yl)methyl}-3-oxo-2,3-dihydropyridazin-6-yl]-2-phenylpyrazolo[1,5-a]pyridine
IR (Nujol): 1650, 1580 cm$^{-1}$

EXAMPLE 61

3-[2-{5-(1H-Tetrazol-5-yl)pentyl}-3-oxo-2,3-dihydropyridazin-6-yl]-2-phenylpyrazolo[1,5-a]pyridine
IR (Nujol): 1635, 1560 cm$^{-1}$

EXAMPLE 62

3-[2-{6-(1H-Tetrazol-5-yl)hexyl}-3-oxo-2,3-dihydropyridazin-6-yl]-2-phenylpyrazolo[1,5-a]pyridine
IR (Nujol): 1640, 1560 cm$^{-1}$

EXAMPLE 63

3-[2-{7-(1H-Tetrazol-5-yl)heptyl}-3-oxo-2,3-dihydropyridazin-6-yl]-2-phenylpyrazolo[1,5-a]pyridine
IR (Nujol): 1650, 1580 cm$^{-1}$

EXAMPLE 64

3-[2-{8-(1H-Tetrazol-5-yl)octyl}-3-oxo-2,3-dihydropyridazin-6-yl]-2-phenylpyrazolo[1,5-a]pyridine
IR (Nujol): 1635, 1550–1565 (broad) cm$^{-1}$

EXAMPLE 65

3-[2-{9-(1H-Tetrazol-5-yl)nonyl}-3-oxo-2,3-dihydropyridazin-6-yl]-2-phenylpyrazolo[1,5-a]pyridine
IR (Nujol): 1635, 1560, 1535, 1490 cm$^{-1}$

EXAMPLE 66

3-[2-[10-(1H-Tetrazol-5-yl)decyl]-3-oxo-2,3-dihydropyridazin-6-yl]-2-phenylpyrazolo[1,5-a]pyridine
IR (Nujol): 1635, 1560, 1535, 1490 cm$^{-1}$

EXAMPLE 67

3-[2-{12-(1H-Tetrazol-5-yl)dodecyl}-3-oxo-2,3-dihydropyridazin-6-yl]-2-phenylpyrazolo[1,5-a]pyridine
IR (Nujol): 1635, 1560, 1535, 1490 cm$^{-1}$
The following compounds ( EXAMPLE 68 to 76) were obtained according to a similar manner to that of Example 18.

EXAMPLE 68

3-[2-(2-Morpholinoethyl)-3-oxo-2,3-dihydropyridazin-yl]-2-phenylpyrazolo[1,5-a]pyridine hydrochloride
IR (Nujol): 2325, 1670, 1590 cm$^{-1}$

EXAMPLE 69

3-[2-(2-Piperidinoethyl)-3-oxo-2,3-dihydropyridazin-yl]-2-phenylpyrazolo[1,5-a]pyridine hydrochloride
IR (Nujol): 2495, 1660, 1595 cm$^{-1}$

EXAMPLE 70

3-[2-(2-Dimethylaminoethyl)-3-oxo-2,3-dihydropyridazin-6-yl]-2-phenylpyrazolo[1,5-a]pyridine hydrochloride
IR (Nujol): 3520, 3450, 2600, 2370, 1640, 1570 cm$^{-1}$

EXAMPLE 71

3-[2-(3-Dimethylaminopropyl)-3-oxo-2,3-dihydropyridazin-6-yl]-2-phenylpyrazolo[1,5-a]pyridine hydrochloride
IR (Nujol): 2400, 1655, 1590 cm$^{-1}$

EXAMPLE 72

3-[2-(2-Phthalimidoethyl)-3-oxo-2,3-dihydropyridazin-yl]-2-phenylpyrazolo[1,5-a]pyridine IR (Nujol): 1760, 1710, 1660, 1630 cm$^{-1}$

EXAMPLE 73

3-[2-(2-Aminoethyl)-3-oxo-2,3-dihydropyridazin-6-yl]-phenylpyrazolo[1,5-a]pyridine IR (Nujol): 3380, 3300, 1660, 1630 cm$^{-1}$

EXAMPLE 74

3-[2-{2-(Ethoxycarbonylmethylamino)ethyl}-3-oxo-2,3-dihydropyridazin-6-yl]-2-phenylpyrazolo[1,5-a]pyridine IR (Nujol): 2750, 2170, 2120, 2430, 1760, 1650, 1630 cm$^{-1}$

EXAMPLE 75

3-[2-{2-(Carboxymethylamino)ethyl}-3-oxo-2,3-dihydro-pyridazin-6-yl]-2-phenylpyrazolo[1,5-a]pyridine IR (Nujol): 3400, 1650, 1600 cm$^{-1}$

EXAMPLE 76

3-[2-{2-{2-Hydroxy-3-(1-naphthyloxy)-propylamino}-ethyl}-3-oxo-2,3-dihydropyridazin-6-yl]-2-phenylpyrazolo-[1,5-a]pyridine NMR (CDCl$_3$, δ) 2.0–3.0 (2H, broad m), 2.9–3.1 (2H, m), 3.1–3.4 (2H, m), 4.0–4.3 (3H, m), 4.3–4.6 (2H, m), 6.7–6.8 (2H, m), 6.8–6.9 (1H, m), 6.98 (1H, d, J=10Hz), 7.0–7.5 (8H, m), 7.5–7.6 (2H, m), 7.7–7.8 (1H, m), 7.9–8.0 (1H, m), 8.1–8.2 (1H, m), 8.4–8.5 (1H, m)

What we claim is:

1. A pyrazolopyridine compound of the formula:

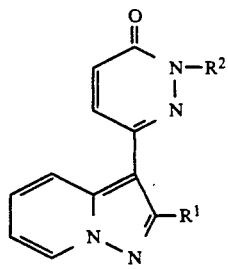

wherein R$^1$ is phenyl, and

R$^2$ is amino(lower)alkyl; lower alkylamino(lower)alkyl; di(lower)alkylamino(lower)alkyl; carboxy(lower)alkylamino(lower)alkyl; protected carboxy(lower)alkylamino(lower)alkyl; lower alkylamino(lower)alkyl substituted by hydroxy and naphthyloxy; protected amino(lower)alkyl; cyano(lower)alkyl; cyano(higher)alkyl; heterocyclic substituted (lower)alkyl wherein heterocyclic is a substituted or unsubstituted heterocyclic group selected from the group consisting of pyridyl, tetrazolyl, piperidyl, piperazinyl, morpholinyl, oxazolidinyl and tetrahydropyranyl, in which said substituent(s) are 1 to 3 substituents independently selected from the group consisting of hydroxy(lower)alkyl, phenyl, (lower)alkoxyphenyl, and oxo; tetrazolyl(higher)alkyl; substituted tetrazolyl(higher)alkyl wherein the substituent is selected from the group consisting of hydroxy(lower)alkyl, oxo, phenyl, and (lower)alkoxyphenyl; phenyl(lower)alkyl; lower alkenyl; or dihydrochromenyl which is unsubstituted or substituted by 1 to 4 substituent(s) independently selected from the group consisting of lower alkyl, hydroxy and cyano, and wherein (lower)alkyl has 1 to 6 carbon atoms and (higher)alkyl has 7 to 20 carbon atoms.

2. A compound of claim 1, wherein
R$^2$ is lower alkylamino(lower)alkyl; tetrazolyl(lower)alkyl; piperidyl(lower)alkyl; morpholinyl(lower)alkyl; or tetrazolyl(higher)alkyl.

3. A pharmaceutical composition which comprises, as an active ingredient, a compound of claim 1 or a pharmaceutically acceptable salt thereof in admixture with a pharmaceutically acceptable carrier or excipient.

4. A method for treating and/or preventing hypertension or renal failure which comprises administering a compound of claim 1 or a pharmaceutically acceptable salt thereof to a human being or an animal.

5. A pharmaceutical composition of claim 3 comprising an adenosine antagonist effective amount of said active ingredient.

* * * * *